US008168786B2

(12) United States Patent
Mann et al.

(10) Patent No.: US 8,168,786 B2
(45) Date of Patent: May 1, 2012

(54) RADIOLABELED COMPOUNDS AND USES THEREOF

(75) Inventors: Joseph John Mann, Riverdale, NY (US); J. S. Dileep Kumar, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 717 days.

(21) Appl. No.: 11/823,641

(22) Filed: Jun. 28, 2007

(65) Prior Publication Data

US 2008/0138283 A1 Jun. 12, 2008

Related U.S. Application Data

(63) Continuation-in-part of application No. PCT/US2005/046565, filed on Dec. 22, 2005.

(60) Provisional application No. 60/639,457, filed on Dec. 28, 2004, provisional application No. 60/729,956, filed on Oct. 24, 2005.

(51) Int. Cl.
| | | |
|---|---|---|
| C07D 403/06 | (2006.01) | |
| C07D 403/14 | (2006.01) | |
| A61K 31/53 | (2006.01) | |
| A61B 8/13 | (2006.01) | |
| A61P 25/06 | (2006.01) | |
| A61P 25/08 | (2006.01) | |
| A61P 25/18 | (2006.01) | |
| A61P 25/22 | (2006.01) | |
| A61P 25/24 | (2006.01) | |
| A61P 25/28 | (2006.01) | |

(52) U.S. Cl. ........................... 544/182; 514/242
(58) Field of Classification Search .................. 544/182; 514/242
See application file for complete search history.

(56) References Cited

U.S. PATENT DOCUMENTS

| | | | |
|---|---|---|---|
| 5,609,849 A | 3/1997 | Kung | |
| 5,859,014 A | 1/1999 | Bantle et al. | |
| 5,977,106 A | 11/1999 | Patoiseau et al. | |
| 2005/0187226 A1 | 8/2005 | Wilson et al. | |

FOREIGN PATENT DOCUMENTS

| | | |
|---|---|---|
| WO | WO-2006/083424 A2 | 8/2006 |
| WO | WO-2009/006227 | 1/2009 |

OTHER PUBLICATIONS

Pimlott SL., Nucl. Med. Commun. 26(3): 183-188, 2005 (PubMed Abstract provided).*
International Search Report and Written Opinion for corresponding International Patent Application No. PCT/US2008/068408.
International Search Report for International Application No. PCT/US2005/046565.
Aznavour et al., "A comparison of in vivo and in vitro neuroimaging of 5-HT$_{1A}$ receptor binding sites in the cat brain," Journal of Chemical Neuroamatomy, vol. 31, pp. 226-232 (2006).
Bailer et al., "Altered Brain Serotonin 5-HT$_{1A}$ receptor binding after recovery from anorexia nervosa measured by positron emission tomography and [Carbonyl$^{11C]WAY-100635}$]," Arch Gen Psychiatry, vol. 62, pp. 1032-1041 (2005).
Bonne et al., "No change in Serotonin type 1A receptor binding in Patients with posttraumatic stress disorder," Am J. Psychiatry, vol. 162, pp. 383-385 (2005).
Cleare et al., "Brain 5-HT$_{1A}$ Receptor binding in chronic fatigue syndrome measured using positron emission tomography and [$^{11}$C]Way-100635," Biol psychiatry, vol. 57, pp. 239-246 (2005).
Derry et al., "Increased serotonin receptor availability in human sleep: Evidence from an [$^{18}$F]MPPF study in narcolepsy," NeuroImage, vol. 30, pp. 341-348 (2006).
Doder et al., "Tremor in Parkinson's disease and serotonergic dysfunction: An 11C-WAY 100635 PET study," Neurology, vol. 60, pp. 601-605 (2003).
Drevets et al., "PET imaging of Serotonin 1A Receptor binding in Depression," Biol Psychiatry, vol. 46, pp. 1375-1387 (1999).
Giovacchini et al., "5-HT$_{1A}$ Receptor are reduced in temporal lobe epilepsy after partial-Volume correction," The journal of Nuclear Medicine, vol. 46, pp. 1128-1135 (Jul. 2005).
Ito et al., Changes in central 5-HT1A receptor binding in mesial temporal epilepsy measured by positron emission tomography with [11C]WAY100635, Epilepsy Res. vol. 73, pp. 111-118 (2007).
Kepe et al., "Serotonin 1A receptors in the living brain of Alzheimer's disease patients," PNAS, vol. 103, pp. 702-707 (Jan. 2006).
Kumar et al., "PET tracers for 5-HT1a receptors and uses thereof," Drug Discovery today, vol. 12, pp. 748-756 (2007). Kumar et al., "Synthesis and in vivo evaluation of a novel 5-HT$_{1A}$ receptor agonist radioligand [O-methyl-$^{11}$C]2-(4-(4-(2-methoxyphenyl) piperazin-1-yl)butyl)-4-methyl-1,2,4-triazine-3, 5(2H,4H)dione in nonhuman primates," Eur. J. Nucl. Med. Mol. Imaging, vol. 34, pp. 1050-1060 (2007).
Lanzenberger et al., "Reduced Serotonin-1A Receptor Binding in Social Anxiety Disorder," Biol Psychiatry, vol. 61, pp. 1081-1089 (2007).
Meltzer et al., "Serotonin IA Receptor binding and treatment response in late-life depression," Neuropsychopharmacology, vol. 29, pp. 2258-2265 (2004).
Merlet et al., "5-HT$_{1A}$ receptor binding and intracerebral activity in temporal lobe epilepsy: an [$^{18}$F]MPPF-PET study," Brain, vol. 127, pp. 900-913 (2004).
Meschaks et al., "Regional Reductions on Serotonin 1A Receptor binding in Juvenile Myoclonic Epilepsy," Arch. Neurol. vol. 62, pp. 946-950 (2005).
Neumeister et al., "Reduced serotonin type $1_A$ Receptor binding in panic disorder," The Journal of Neuroscience, vol. 24(3); pp. 589-591 (2004).
Parsey et al., "Altered Serotonin 1A Binding in major Depression: A [carbonyl-C-11]WAY100635 positron emission tomography study," Biol Psychiatry, vol. 59, pp. 106-113 (2006).

(Continued)

*Primary Examiner* — Venkataraman Balasubramanian
(74) *Attorney, Agent, or Firm* — Wilmer Cutler Pickering Hale and Dorr LLP

(57) ABSTRACT

The present invention relates to Radiolabeled Compounds and methods of use thereof for treating or preventing a psychiatric disorder in a subject, for stabilizing the mood of a subject having a mood disorder, or as imaging agents for a serotonin receptor. Compositions comprising an imaging-effective amount of a Radiolabeled Compound are also disclosed.

37 Claims, No Drawings

OTHER PUBLICATIONS

Parsey et al., "Higher 5-HT$_{1A}$ Receptor binding potential during a major depressive episode predicts poor treatment response: Preliminary data from a Naturalistic study," Neuropsychopharmacology, vol. 31, pp. 1745-1749 (2006).

Price et al., "Evidence of increased serotonin-IA receptor binding in type 2 diabetes: a positron emission tomography study," Brain Research, vol. 927, pp. 97-103 (2002).

Savic et al., "Limbic reductions of 5-HT$_{1A}$ receptor binding in human temporal lobe epilepsy," Neurology, vol. 62, pp. 1343-1351 (2004).

Sullivan et al., "Brain Serotonin $_{1A}$ Receptor binding in major depression is related to Psychic and somatic anxiety," Biol Psychiatry, vol. 58, pp. 947-954 (2005).

Tauscher et al., "Brain Serotonin 5-HT$_{1A}$ receptor binding in schizophrenia measured by positron emission tomography and [$^{11}$C]WAY-100635," Arch Gen Psychiatry, vol. 59, pp. 514-520 (2002).

Theodore et al., "The Effect of Antiepileptic drugs on 5-HT$_{1A}$- Receptor binding measured by positron emission tomography," Epilepsia, vol. 47(3), pp. 499-503 (2006).

Tiihonen et al., "Brain Serotonin 1A Receptor binding in Bulimia nervosa," Biol Psychiatry, vol. 55, pp. 871-873 (2004).

Turner et al., "[$^{11}$C]-way 100635 PET demonstrates marked 5-HT$_{1A}$ receptor changes in sporadic ALS," Brain, vol. 128, pp. 896-905 (2005).

Udo de Haes et al., "Effect of Fenfluramine-Induced Increases in Serotonin Release on [18F]MPPF Binding: A Continuous Infusion PET Study in Conscious Monkeys," Synapse, vol. 59, pp. 18-26 (2006).

Weiss et al., "Language lateralization in unmedicated patients during an acute episode of schizophrenia: A Functional MRI Study," Psychiatry Research: Neuroimaging, vol. 146, pp. 185-193 (2006).

Yasuno et al., Decreased 5-HT$_{1A}$ Receptor Binding in Amygdala of Schizophrenia, Biol Psychiatry, vol. 55, pp. 439-444 (2004).

Dannon et al., "Pindolol augmentation in treatment-resistant obsessive compulsive disorder: a double-blind placebo controlled trial," European Neuropsychopharmacology, vol. 10, pp. 165-169 (2000).

Woods et al., "Selective Serotonin re-uptake inhibitors decrease schedule-induced poly-dipsia in rats: a potential model for obsessive compulsive disorder," Psychopharmacology, vol. 112, pp. 195-198 (1993).

El Mansari et al., "Responsiveness of 5-HT1A and 5-HT2 receptors in the rat orbitofrontal cortex after long-term serotonin reuptake inhibition," Rev. Psychiatr. Neurosci, vol. 30, pp. 268-274 (2005).

Muller et al., "Serotonin and psychostimulant addiction: Focus on 5-HT1A-receptors," Progress in Neurobiology, vol. 81, pp. 133-178 (2007).

Aouizerate et al., "Updated overview of the putative role of the serotoninergic system in obsessive-compulsive disorder," Neuropsychiatric Disease and Treatment, vol. 1(3); pp. 231-243 (2005).

Blier et al., "The importance of serotonin and noradrenaline in anxiety," International Journal of Psychiatry in Clinical Practice, vol. 11, pp. 16-23 (2007).

Lesch et al., "Long-Term fluoxetine treatment decreases 5-HT1A receptor responsivity in obsessive-compulsive disorder," Psychopharmacology vol. 105; pp. 415-420 (1991).

Brett et al., "Exclusion of the 5-HT1A Serotonin Neuroreceptor and tryptophan Oxygenase Genes in a large British kindred multiply affected with tourette's Syndrome, Chronic motor tics, and obsessive-compulsive behavior," Am. J. Psychiatry, vol. 152; pp. 437-440 (Mar. 1995).

Lesch et al., "5-HT1A receptor responsivity in anxiety disorders and depression," Prog. Neuro-Psychopharmacol & Biol. Psychiat., vol. 15, pp. 723-733 (1991).

Matsushita et al., "Perospirone, a novel antipsychotic drug, inhibits marble-burying behavior via 5-HT1A Receptor in mice: implication for obsessive-compulsive disorder," J. Pharmacol Sci, vol. 99, pp. 154-159 (2005).

Lesch et al.,"5-Hydroxytryptamine1A Receptor responsivity in obsessive-compulsive disorder. Comparison of Patients and Controls," Arch Gen Psychiatry, vol. 48; pp. 540-547 (1991).

Crocq et al., "Cliinical potentialities and perpectives for the use of aripiprazole in other disorders than its classical indications. A critical analysis of the recent literature," L'Encephale, vol. 34, pp. 187-193 (2008) (English Abstract).

Colpaert et al., "5-HT1A receptor in chronic pain processing and control," Proceedings of the World Congress on Pain, 11th, Sydney, Australia, Aug. 21-26, 2005 (2006), Meeting Date, pp. 147-154.

International Search Report and Written Opinion mailed on Jul. 27, 2011 for International Application No. PCT/US11/35385 filed May 5, 2011.

Kumar et al, "Synthesis and in vivo validation of [O-Methyl-$^{11}$-C]2-{4-[4-(7-methoxynaphthalen-1-yl)piperazin-1-yl]butyl}-4-methyl-2H-[1,2,3]traizine-3,5-dione: A novel 5-HT$_{1A}$ Receptor agonist positron emission tomography ligand," J. Med Chem., vol. 49, pp. 125-134 (2006).

Prabhakaran et al., "Synthesis, in vitro and in vivo evolution of [O-methy1-$^{11}$C]2-{4-[4-(3-methoxyphenyl)piperazin-1*-yl]-butyl-4-methyl-2H-[1,2,4]-triazine-3,5-diones: A novel agonist 5-HT$_{1A}$ treceptor PET ligand," Bioorg. Med. Chem. Lett., vol. 16, pp. 2101-2104 (2006).

Milak et al., "Modeling considerations for $^{11}$C-CUMI-101, an agonist radiotracer for imaging serotonin 1A Receptor in vivo with PET," J. Nucl. Med, vol. 49, pp. 587-596 (2008).

Milak et al., "In vivo serotonin-sensitive binding of [$^{11}$C]CUMI-101: a seotonin 1A receptor agonist positron emission tomography radiotracer," J. of Cerebral Blood Flow & metabolism, vol. 31, pp. 243-249 (2001).

Milak et al., "In vivo quantification of human serotonin 1A receptor using $^{11}$C-CUMI-101, an agonist PET Radiotracer," The Journal of Nuclear medicine, vol. 51, pp. 1892-1900 (2010).

Majo et al., "Synthesis and evaluation of [O-methyl-$^{11}$C]4-[3-[4-(2-methoxyphenyl)-piperazin-1-yl]propoxy]-4-aza-tricyclo[5.2.1.02,6]dec-8-ene-3,5-dione as a 5-HT$_{1A}$ receptor agonist PET ligand," Journal of labelled Compounds and Radiopharmaceuticals, vol. 51, pp. 132-136 (2008).

* cited by examiner

RADIOLABELED COMPOUNDS AND USES THEREOF

This application is a continuation-in-part of International Application No. PCT/US2005/046565, filed on Dec. 22, 2005, now published as WO 2006/083424, which claims priority to U.S. Provisional Application No. 60/639,457, filed Dec. 28, 2004, and a U.S. Provisional Application No. 60/729,956, filed Oct. 24, 2005, the contents of which are incorporated by reference herein in their entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention relates to Radiolabeled Compounds and methods of use thereof for treating or preventing a psychiatric disorder in a subject, for stabilizing the mood of a subject having a mood disorder, or as imaging agents for a serotonin receptor. Compositions comprising an imaging-effective amount of a Radiolabeled Compound are also disclosed.

BACKGROUND OF THE INVENTION

Powerful imaging methods currently exist which enable one to assess the living brain and body in vivo and thereby monitor the effectiveness of treatments that affect brain chemistry and function. Positron emission tomography (PET) is a dynamic, non-invasive imaging technique used in nuclear medicine to study various biochemical and biological process in vivo. In PET, labeled compounds may be administered in nanomolar or picomolar concentrations, allowing imaging studies to be performed without perturbing the biological system being studied. These labeled compounds may generally be radioisotopes that give off positrons. The emitted positrons may then collide with electrons, which generates gamma rays. The emitted gamma rays may then be detected by scanners and be processed to obtain images of the living brain and body. Like other dynamic imaging protocols, PET has the ability collect images repeatedly over time and provide information about regional distribution of the tracer as well as the change in compartmental distribution as a function of time. As such, PET lends itself directly to measuring kinetic processes, such as rate of tracer uptake by cells, substrate metabolic rates, receptor density/affinity, and regional blood flow.

Serotonin system in the brain is an important neurotransmission network regulating various physiological functions and behavior including anxiety and mood states. Serotonin (5-hydroxytryptamine; 5-HT) has been linked with major depression, bipolar disorder, eating disorders, alcoholism, pain, anxiety, obsessive-compulsive disorders, Alzheimer's Disease, Parkinson's disease and other psychiatric maladies. It is also involved in mediating the action of many psychotropic drugs including antidepressants, antianxiety drugs and antipsychotics. There are more than a dozen known subtypes of serotonin receptors. Among these serotonin receptors, 5-HT$_{1A}$ receptors play a role as a presynaptic autoreceptor in the dorsal raphe nucleus and as a postsynaptic receptor for serotonin in terminal field areas.

Several radioligands for 5-HT$_{1A}$ receptors have been prepared and evaluated. The most successful radioligands studied so far for 5-HT$_{1A}$ receptors are antagonist tracers which bind with both the G-protein-coupled high affinity (HA) state and uncoupled low affinity (LA) state of 5-HT$_{1A}$ receptors. In contrast, agonists bind preferentially to the HA state of the 5-HT$_{1A}$ receptor. Therefore, having a radioligand agonist tracer may provide a more meaningful functional measure of 5-HT$_{1A}$ receptors. To date there are no successful 5-HT$_{1A}$ agonist radiotracers available for studies in a living brain.

Thus, there is still a need in the art for radiolabeled serotonin agonist modulators that are highly selective for imaging 5-HT$_{1A}$ receptors. Moreover, there remains a need in the art for selective radioactive tracers, which are useful for imaging 5-HT$_{1A}$ receptors in vivo. The present invention addresses these needs.

SUMMARY OF THE INVENTION

In one aspect, the present invention provides Radiolabeled Compounds having the Formula (I):

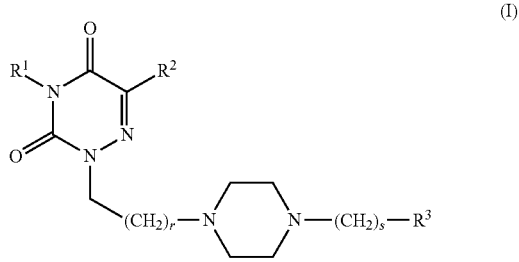

or a pharmaceutically acceptable salt thereof,
wherein:
r and s are each independently an integer ranging from 0 to 6;
R$^1$ is H, aryl, C$_1$-C$_6$ alkyl, C$_3$-C$_7$ cycloalkyl, C$_3$-C$_7$ cycloalkenyl, 3- to 7-membered heterocycle, $^{11}$C-labeled C$_1$-C$_6$ alkylene, $^{11}$C-labeled C$_2$-C$_6$ alkenylene, $^{11}$C-labeled C$_2$-C$_6$ alkynylene, $^{18}$F-labeled C$_1$-C$_6$ alkylene, $^{18}$F-labeled C$_2$-C$_6$ alkenylene, or $^{18}$F-labeled C$_2$-C$_6$ alkynylene alkyne;
R$^2$ is H, aryl, C$_1$-C$_6$ alkyl, C$_3$-C$_7$ cycloalkyl, C$_3$-C$_7$ cycloalkenyl, 3- to 7-membered heterocycle, halo, CF$_3$, C$_2$-C$_6$ alkenyl, C$_2$-C$_6$ alkynyl, N(R$^4$)$_2$, CN, OR$^4$ or SR$^4$;
R$^3$ is aryl or 5- to 7-membered aromatic heterocycle, each of which is substituted with one R$^6$ group and optionally substituted with one or more of the following groups: C$_1$-C$_6$ alkyl, C$_3$-C$_7$ cycloalkyl, C$_3$-C$_7$ cycloalkenyl or 3- to 7-membered heterocycle, halo, CF$_3$, C$_2$-C$_6$ alkenyl, C$_2$-C$_6$ alkynyl, (C$_1$-C$_6$ alkylene)-aryl, N(R$^4$)$_2$, CN, OR$^4$, SR$^4$, S(O)—R$^4$, SO$_2$—R$^4$, SO$_2$NH—R$^4$, SO$_3$H, NH—SO$_2$—R$^4$, C(O)R$^5$ or NHC(O)R$^5$;
each occurrence of R$^4$ is independently H, C$_1$-C$_6$ alkyl, C$_1$-C$_6$ fluoroalkyl, C$_2$-C$_6$ alkenyl, C$_2$-C$_6$ alkynyl, aryl, (C$_1$-C$_6$ alkylene)-aryl, C$_3$-C$_7$ cycloalkyl, C$_3$-C$_7$ cycloalkenyl or 3- to 7-membered heterocycle;
R$^5$ is R$^4$, N(R$^4$)$_2$ or OR$^4$;
R$^6$ is L-M-Q;

L is a single bond, O, S, NH, F, $^{18}$F, $CF_3$, $^{18}$F-labeled $CF_3$, $CF_2H$, $^{18}$F-labeled $CF_2H$, or $^{11}$C-labeled CN;

M is $^{11}$C-labeled $C_1$-$C_6$ alkylene, $^{11}$C-labeled $C_2$-$C_6$ alkenylene, $^{11}$C-labeled $C_2$-$C_6$ alkynylene, $^{18}$F-labeled $C_1$-$C_6$ alkylene, $^{18}$F-labeled $C_2$-$C_6$ alkenylene, or $^{18}$F-labeled $C_2$-$C_6$ alkynylene; and Q is H or aryl.

In another aspect, the present invention provides Radiolabeled Compounds having the Formula (II):

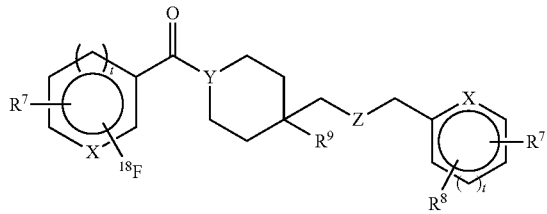

(II)

or a pharmaceutically acceptable salt thereof,
wherein:

each $R^7$ is independently —H, -halo, —$C_1$-$C_6$ alkyl, —$C_1$-$C_6$ fluoroalkyl, —$C_3$-$C_7$ cycloalkyl, —$C_3$-$C_7$ cycloalkenyl, —$C_2$-$C_6$ alkenyl, —$C_2$-$C_6$ alkynyl, —$N(R^{10})_2$, —CN, —$OR^{10}$, —$SR^{10}$, —S(O)—$R^{10}$, —$SO_2$—$R^{10}$, —$SO_2NH$—$R^{10}$, —$SO_3H$, —NH—$SO_2$—$R^{10}$, —C(O)$R^{11}$, —NHC(O)$R^{11}$, -aryl, -3- to 7-membered heterocycle, -alkoxycarbonyl, or

$R^8$ is —$Z^a$—$R^{12}$, —H, -halo, —$C_1$-$C_6$ alkyl, -fluoroalkyl, —$C_3$-$C_7$ cycloalkyl, —$C_3$-$C_7$ cycloalkenyl, —$C_2$-$C_6$ alkenyl, —$C_2$-$C_6$ alkynyl, —$N(R^{10})_2$, —CN, —$OR^{10}$, —$SR^4$, —S(O)—$R^{10}$, —$SO_2$—$R^{10}$, —$SO_2NH$—$R^{10}$, —$SO_3H$, —NH—$SO_2$—$R^{10}$, —C(O)$R^{11}$, —NHC(O)$R^{11}$, -aryl, -3- to 7-membered heterocycle, -alkoxycarbonyl, or

$R^9$ is —H or -halo;

each $R^{10}$ is independently —H, —$C_1$-$C_6$ alkyl, —$C_1$-$C_6$ fluoroalkyl, —$C_2$-$C_6$ alkenyl, —$C_2$-$C_6$ alkynyl, -aryl, —($C_1$-$C_6$ alkylene)-aryl, —$C_3$-$C_7$ cycloalkyl, —$C_3$-$C_7$ cycloalkenyl or -3- to 7-membered heterocycle;

$R^{11}$ is —$R^4$, —$N(R^4)_2$ or —$OR^4$;

$R^{12}$ is —$^{11}$C-labeled $C_1$-$C_6$ alkyl, —$^{11}$C-labeled $C_2$-$C_6$ alkenyl, —$^{11}$C-labeled $C_2$-$C_6$ alkynyl, —($^{11}$C-labeled $C_1$-$C_6$ alkylene)-aryl, —($^{11}$C-labeled $C_2$-$C_6$ alkenylene)-aryl, or —($^{11}$C-labeled $C_2$-$C_6$ alkynylene)-aryl;

each X is independently —CH—, —N—, —S—, or —O—;

Y is —CH— or —N—;

Z is —$CH_2$—, —NH—, —S—, or —O—;

$Z^a$ is —O—, —S—, or —NH—;

t is 0 or 1, such that t is zero when X is —S—; and u is 1 or 2.

The Compounds of Formula (I) and Formula (II) (the "Radiolabeled Compounds") are useful for: (i) detecting in vivo 5-$HT_{1A}$ receptors in a subject; (ii) treating or preventing a psychiatric disorder in a subject, or (iii) stabilizing the mood of a subject having a mood disorder.

In yet another aspect, the present invention provides a method for detecting in vivo 5-$HT_{1A}$ receptors in a subject, the method comprising:

(a) administering to the subject an imaging-effective amount of a Radiolabeled Compound or a pharmaceutically acceptable salt thereof, and (b) detecting the radioactive emission of the compound or salt thereof administered to the subject.

In yet another aspect, the present invention provides a method for detecting in vivo 5-$HT_{1A}$ receptors in a subject, the method comprising:

(a) administering to the subject an imaging-effective amount of a Radiolabeled Compound or a pharmaceutically acceptable salt thereof, and (b) detecting the radioactive emission of the compound or salt thereof administered to the subject.

In the present methods, the radioactive emissions from the $^{11}$C- and/or $^{18}$F-atom of a Radiolabeled Compound can be detected using PET for imaging one or more 5-$HT_{1A}$ serotonin receptors in a subject. The radioactive emission can be detected anywhere in the body of the subject. In one embodiment, the radioactive emission is detected in the brain of the subject. In a further embodiment, the subject can be known or suspected to have a psychiatric or neurological disorder.

The invention also relates to compositions comprising a physiologically acceptable carrier or vehicle and an amount of a Radiolabeled Compound that is effective to: (i) treat or prevent a psychiatric disorder in a subject; or (ii) stabilize the mood of a subject having a mood disorder. The compositions are useful for treating or preventing a psychiatric disorder in a subject, or for stabilizing the mood of a subject having a mood disorder.

The present invention may be understood more fully by reference to the following detailed description and illustrative examples, which are intended to exemplify non-limiting embodiments of the invention.

DETAILED DESCRIPTION OF THE INVENTION

Definitions and Abbreviations

The terms used herein having following meanings:

The term "alkyl" as used herein, refers to a straight chain or branched non-cyclic hydrocarbon, wherein one of the hydrocarbon's hydrogen atoms has been replaced with a single bond. Hence, the term "$C_1$-$C_6$ alkyl" as used herein, refers to a straight chain or branched non-cyclic hydrocarbon having from 1 to 6 carbon atoms, wherein one of the hydrocarbon's hydrogen atoms has been replaced with a single bond. Representative straight chain $C_1$-$C_6$ alkyls include methyl, ethyl, n-propyl, n-butyl, n-pentyl, and n-hexyl. Representative branched $C_1$-$C_6$ alkyls include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, isopropyl, sec-butyl, isobutyl, neohexyl, isohexyl, and the like. In certain embodiments, the $C_1$-$C_6$ alkyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted C$_1$-C$_6$ alkyl.

The term "fluoroalkyl" as used herein, refers to a C$_1$-C$_6$ alkyl group wherein one or more of the C$_1$-C$_6$ alkyl group's hydrogen atoms have been replaced with a fluorine atom. Representative fluoroalkyls include monofluoromethyl —CHF$_2$, —CH$_2$F, —CF$_3$, —CH(F)CH$_3$, or —CF$_2$CH$_3$. In certain embodiments, the fluoroalkyl may be substituted with one or more of the following groups: halo, O—(C$_1$-C$_6$ alkyl), OH, CN, COOR', OC(O)R', N(R')$_2$, NHC(O)R' or C(O)NHR' groups wherein each R' is independently H or unsubstituted C$_1$-C$_6$ alkyl.

The term "alkenyl" as used herein, refers to a straight chain or branched non-cyclic hydrocarbon including at least one carbon-carbon double bond, wherein one of the hydrocarbon's hydrogen atoms has been replaced with a single bond. Hence, the term "C$_2$-C$_6$ alkenyl" as used herein, refers to a straight chain or branched non-cyclic hydrocarbon having from 2 to 6 carbon atoms and including at least one carbon-carbon double bond, wherein one of the hydrocarbon's hydrogen atoms has been replaced with a single bond. Representative straight chain and branched C$_2$-C$_6$ alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, and the like. In certain embodiments, the C$_2$-C$_6$ alkenyl may be substituted with one or more of the following groups: halo, O—(C$_1$-C$_6$ alkyl), OH, CN, COOR', OC(O)R', N(R')$_2$, NHC(O)R' or C(O)NHR' groups wherein each R' is independently H or unsubstituted C$_1$-C$_6$ alkyl.

The term "alkynyl" as used herein, refers to a straight chain or branched non-cyclic hydrocarbon including at lease one carbon-carbon triple bond, wherein one of the hydrocarbon's hydrogen atoms has been replaced with a single bond. Hence, the term "C$_2$-C$_6$ alkynyl" as used herein, refers to a straight chain or branched non-cyclic hydrocarbon having from 2 to 6 carbon atoms and including at lease one carbon-carbon triple bond, wherein one of the hydrocarbon's hydrogen atoms has been replaced with a single bond. Representative straight chain and branched C$_2$-C$_6$ alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like. In certain embodiments, the C$_2$-C$_6$ alkynyl may be substituted with one or more of the following groups: halo, O—(C$_1$-C$_6$ alkyl), OH, CN, COOR', OC(O)R', N(R')$_2$, NHC(O)R' or C(O)NHR' groups wherein each R' is independently H or unsubstituted C$_1$-C$_6$ alkyl.

The term "alkylene" as used herein, refers to a straight chain or branched non-cyclic hydrocarbon, wherein two of the hydrocarbon's hydrogen atoms have been replaced with a single bond. Hence, the term "C$_1$-C$_6$ alkylene" as used herein, refers to a straight chain or branched non-cyclic hydrocarbon having from 1 to 6 carbon atoms, wherein two of the hydrocarbon's hydrogen atoms have been replaced with a single bond.

A "$^{11}$C-labeled C$_1$-C$_6$ alkylene group" is a C$_1$-C$_6$ alkylene group, as defined above, wherein one of the C$_1$-C$_6$ alkylene group's carbon atoms has been replaced with a $^{11}$C isotope. A "$^{11}$C-labeled C$_1$-C$_6$ alkyl group" is a C$_1$-C$_6$ alkyl group, as defined above, wherein one of the C$_1$-C$_6$ alkyl group's carbon atoms has been replaced with a $^{11}$C isotope. Representative $^{11}$C-labeled C$_1$-C$_6$ alkylene groups include, but are not limited to $^{11}$CH$_2$, CH$_2$$^{11}$CH$_2$, CH$_2$CH$_2$$^{11}$CH$_2$, CH$_2$CH$_2$CH$_2$$^{11}$CH$_2$, CH$_2$CH$_2$CH$_2$CH$_2$$^{11}$CH$_2$, and CH$_2$CH$_2$CH$_2$CH$_2$CH$_2$$^{11}$CH$_2$.

A "$^{18}$F-labeled C$_1$-C$_6$ alkylene group" is a C$_1$-C$_6$ alkyl group, as defined above, wherein one of the C$_1$-C$_6$ alkyl group's hydrogen atoms has been replaced with a $^{18}$F isotope.

The term "alkenylene" as used herein, refers to a straight chain or branched non-cyclic hydrocarbon including at least one carbon-carbon double bond, wherein two of the hydrocarbon's hydrogen atoms have been replaced with a single bond. Hence, the term "C$_2$-C$_6$ alkenylene" as used herein, refers to a straight chain or branched non-cyclic hydrocarbon having from 2 to 6 carbon atoms and including at least one carbon-carbon double bond, wherein two of the hydrocarbon's hydrogen atoms have been replaced with a single bond.

A "$^{11}$C-labeled C$_2$-C$_6$ alkenylene group" is a C$_2$-C$_6$ alkenylene group, as defined above, wherein one of the C$_2$-C$_6$ alkenylene group's carbon atoms has been replaced with a $^{11}$C isotope.

A "$^{18}$F-labeled C$_2$-C$_6$ alkenylene group" is a C$_2$-C$_6$ alkenylene group, as defined above, wherein one of the C$_2$-C$_6$ alkenylene group's hydrogen atoms has been replaced with a $^{18}$F isotope.

The term "alkynylene" as used herein, refers to a straight chain or branched non-cyclic hydrocarbon including at lease one carbon-carbon triple bond, wherein two of the hydrocarbon's hydrogen atoms have been replaced with a single bond. Hence, the term "C$_2$-C$_6$ alkynylene" as used herein, refers to a straight chain or branched non-cyclic hydrocarbon having from 2 to 6 carbon atoms and including at lease one carbon-carbon triple bond, wherein two of the hydrocarbon's hydrogen atoms have been replaced with a single bond.

A "$^{11}$C-labeled C$_2$-C$_6$ alkynylene group" is a C$_2$-C$_6$ alkynylene group, as defined above, wherein one of the C$_2$-C$_6$ alkynylene group's carbon atoms has been replaced with a $^{11}$C isotope.

A "$^{18}$F-labeled C$_2$-C$_6$ alkynylene group" is a C$_2$-C$_6$ alkynylene group, as defined above, wherein one of the C$_2$-C$_6$ alkynylene group's hydrogen atoms has been replaced with a $^{18}$F isotope.

The term "alkoxycarbonyl" means a moiety of the formula —COOR', where R' is independently H or unsubstituted C$_1$-C$_6$ alkyl. Examples of such alkoxycarbonyl include methoxycarbonyl, ethoxycarbonyl, and the like.

The term "aryl" as used herein refers to a phenyl group, a biphenyl group, biphenylene group, anthracene group, fulvene group, phenanthrene group, or a naphthyl group. In certain embodiments, the aryl group may be substituted with one or more of the following groups: halo, O—C$_1$-C$_6$ alkyl, O—C$_2$-C$_6$ alkenyl, O—C$_2$-C$_6$ alkynyl, OH, CN, COOR', OC(O)R', N(R')$_2$, NHC(O)R', S—(C$_1$-C$_6$ alkyl or alkenyl or alkynyl), S—(O)—C$_1$-C$_6$ alkyl, S(O)—C$_2$-C$_6$ alkenyl, S(O)—C$_2$-C$_6$ alkynyl, S—(O$_2$)—C$_1$-C$_6$ alkyl, S(O$_2$)—C$_2$-C$_6$ alkenyl, S(O)—C$_2$-C$_6$ alkynyl, or C(O)NHR' groups wherein each R' is independently —H or unsubstituted —C$_1$-C$_6$ alkyl.

The term "cycloalkyl" as used herein refers to a saturated non-aromatic monocyclic cycloalkyl ring. Hence, the term "C$_3$-C$_7$ cycloalkyl" as used herein refers to a 3-, 4-, 5-, 6- or 7-membered saturated non-aromatic monocyclic cycloalkyl ring. Representative C$_3$-C$_7$ monocyclic cycloalkyl groups include, but are not limited to, cyclopropyl, cyclobutyl, cyclopentyl, cyclohexyl and cycloheptyl. In certain embodiments, the aryl group may be substituted with one or more of the following groups: halo, O—C$_1$-C$_6$ alkyl, O—C$_2$-C$_6$ alkenyl, O—C$_2$-C$_6$ alkynyl, OH, CN, COOR', OC(O)R', N(R')$_2$, NHC(O)R', S—(C$_1$-C$_6$ alkyl or alkenyl or alkynyl), S—(O)—C$_1$-C$_6$ alkyl, S(O)—C$_2$-C$_6$ alkenyl, S(O)—C$_2$-C$_6$ alkynyl, S—(O)—C$_1$-C$_6$ alkyl, S(O$_2$)—C$_2$-C$_6$ alkenyl, S(O$_2$)—C$_2$-C$_6$ alkynyl, or C(O)NHR' groups wherein each R' is independently H or unsubstituted C$_1$-C$_6$ alkyl.

The term "cycloalkenyl" as used herein refers to non-aromatic monocyclic carbocyclic ring having at least one endocyclic double bond. Hence, the term "$C_3$-$C_7$ cycloalkenyl" as used herein refers to a 3-, 4-, 5-, 6- or 7-membered non-aromatic monocyclic carbocyclic ring having at least one endocyclic double bond, but which is not aromatic. It is to be understood that when any two groups, together with the carbon atom to which they are attached form a $C_3$-$C_7$ monocyclic cycloalkenyl group, the carbon atom to which the two groups are attached remain tetravalent. Representative $C_3$-$C_7$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl and -1,3,5-cycloheptatrienyl. In one embodiment, the aryl group is substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—(O$_2$)—$C_1$-$C_6$ alkyl, S(O$_2$)—$C_2$-$C_6$ alkenyl, S(O$_2$)—$C_2$-$C_6$ alkynyl, or C(O)NHR' groups wherein each R' is independently H or unsubstituted $C_1$-C6 alkyl.

The term "halo" as used herein, refers to F, Cl, Br, or I.

The term "3- to 7-membered heterocycle" refers to: (i) a 3- or 4-membered non-aromatic monocyclic cycloalkyl in which 1 of the ring carbon atoms has been replaced with a N, O or S atom; (ii) a 5-, 6-, or 7-membered aromatic or non-aromatic monocyclic cycloalkyl in which 1-4 of the ring carbon atoms have been independently replaced with a N, O or S atom. The term 3- to 7-membered heterocycle also encompasses any heterocycles described by (i) or (ii) which are fused to a benzene ring, or in which any one of the ring carbon atoms comprises a carbonyl group, such as in lactam and lactone ring systems. The non-aromatic 3- to 7-membered heterocycles can be attached via a ring nitrogen, sulfur, or carbon atom. The aromatic 3- to 7-membered heterocycles are attached via a ring carbon atom. Representative examples of a 3- to 7-membered heterocycle group include, but are not limited to, dihydrofuran-2-one, dihydrofuranyl, furanyl, benzofuranyl, furazanyl, imidazolidinyl, imidazolinyl, imidazolyl, benzimidazolyl, indazolyl, indolinlyl, indolyl, indolizinyl, isoindolinyl, isothiazolyl, isoxazolyl, benzisoxazolyl, morpholinyl, oxadiazolyl, oxazolidinyl, oxazolyl, benzoxazolyl, oxazolidinyl, pyrimidinyl, phenanthridinyl, phenanthrolinyl, piperazinyl, piperidinyl, pyranyl, benzopyranyl, pyrazinyl, pyrazolidinyl, pyrazolinyl, pyrazolyl, pyridazinyl, pyridooxazole, pyridoimidazole, pyridothiazole, pyridyl, pyrimidinyl, pyrrolidinyl, pyrrolinyl, quinolinyl, isoquinolinyl, quinoxalinyl, phthalazinyl, cinnolinyl, quinolizinyl, quinazolinyl, quinuclidinyl, tetrahydrofuranyl, thiadiazinyl, thiadiazolyl, thiazolyl, benzthiazolyl, thienyl, thienothiazolyl, thienooxazolyl, thienoimidazolyl, thiomorpholinyl, thiophenyl, benzothiphenyl, triazinyl, and triazolyl. In one embodiment, the 3- to 7-membered heterocycle group is substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "5- to 7-membered aromatic heterocycle" refers to a 5-, 6-, or 7-membered aromatic monocyclic cycloalkyl in which 1-4 of the ring carbon atoms have been independently replaced with a N, O or S atom. The term 5- to 7-membered aromatic heterocycle also encompasses any heterocycles described which are fused to a benzene ring, or in which any one of the ring carbon atoms comprises a carbonyl group, such as in lactam and lactone ring systems. The 5- to 7-membered aromatic heterocycles are attached via a ring carbon atom. Representative examples of a 5- to 7-membered aryl heterocycle group include, but are not limited to, furanyl, benzofuranyl, furazanyl, imidazolyl, benzimidazolyl, indazolyl, indolyl, indolizinyl, isoindolinyl, isothiazolyl, isoxazolyl, benzisoxazolyl, oxadiazolyl, oxazolidinyl, oxazolyl, benzoxazolyl, oxazolidinyl, pyrimidinyl, phenanthridinyl, phenanthrolinyl, pyranyl, benzopyranyl, pyrazinyl, pyrazolyl, pyridazinyl, pyridooxazole, pyridoimidazole, pyridothiazole, pyridyl, pyrimidinyl, quinolinyl, isoquinolinyl, quinoxalinyl, phthalazinyl, cinnolinyl, quinolizinyl, quinazolinyl, thiadiazinyl, thiadiazolyl, thiazolyl, benzthiazolyl, thienyl, thienothiazolyl, thienooxazolyl, thienoimidazolyl, thiophenyl, and benzothiphenyl. In certain embodiments, the 5- to 7-membered aromatic heterocycle group may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "imaging-effective amount" when used in connection with a Radiolabeled Compound of the present invention or pharmaceutically acceptable salt thereof, is an amount of the compound that is sufficient to produce a visible image when the compound is administered to a subject and the radiation emitted by the compound is detected using positron-emission tomography ("PET") or autoradiography.

The term "isolated" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Radiolabeled Compound of the present invention by weight of the isolate. In one embodiment, the isolate contains at least 95% of a Radiolabeled Compound of the present invention by weight of the isolate.

The phrase "pharmaceutically acceptable salt," as used herein, is a salt of an acid and a basic nitrogen group of a Radiolabeled Compound of the present invention. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt of a Radiolabeled Compound of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as tri-(2-hydroxyethyl) amine or N,N-dimethyl-N-(2-hydroxyethyl)amine; N-methyl-D-glucamine; or amino acids such as arginine, lysine, and the like. The term "pharmaceutically acceptable salt" also includes a hydrate of a Radiolabeled Compound of the present invention.

As used herein, a "5-$HT_{1A}$ selective agent" refers to a compound that can selectively interact with the 5-$HT_{1A}$ receptor relative to the other known transporters, receptors, enzymes and proteins. 5-$HT_{1A}$ selective agents include agonists and antagonists that specifically bind to 5-$HT_{1A}$ receptors.

The term "subject," as used herein, includes, but is not limited to, a non-human animal, such as a cow, monkey, chimpanzee, baboon, horse, sheep, pig, chicken, turkey, quail, cat, dog, mouse, rat, rabbit, or guinea pig; and a human. In one embodiment, a monkey is a rhesus. In another embodiment, a subject is a human.

The term "therapeutically effective amount" when used in connection with a Radiolabeled Compound of the present invention or a pharmaceutically acceptable salt thereof is an amount that is effective to (i) treat or prevent a psychiatric disorder in a subject, or (ii) stabilize the mood of a subject having a mood disorder.

The following abbreviations are used herein and have the indicated definitions: n-BuOH is n-butyl alcohol; DMSO is N,N-dimethylsulfoxide; EtOH is ethanol; $Et_3N$ is triethylamine; Kryptofix® 222 is 4,7,13,16,21,24-hexaoxa-1,10-diazabicyclo[8.8.8]-hexacosane (Acros Organics, Belgium); mCPBA is m-chloroperbenzoic acid; $MeNH_2$ is methylamine; Ms or mesyl is methanesulfonyl; MS is mass spectrometry; NMR is nuclear magnetic resonance; PEG is polyethylene glycol; py is pyridine; TBAH is tetrabutylammonium hydroxide; Ts or tosyl is -p-toluenesulfonyl; TsCl is p-toluenesulfonyl chloride; Tf or triflyl is trifluoromethanesulfonate; and TMSCN is trimethylsilylcyanide.

The Radiolabeled Compounds

The Radiolabeled Compounds of the present invention may be useful as imaging agents for one or more 5-$HT_{1A}$ receptors.

In certain embodiments, the Radiolabeled Compounds of the present invention may have one or more of the following characteristics: (i) high affinity and selectivity for the 5-$HT_{1A}$ receptor compared to the other known transporters, receptors, enzymes and proteins; (ii) sufficient lipophilicity to allow rapid blood-brain-barrier penetration and generation of polar metabolites that do not cross the blood-brain-barrier; and (iii) high specific activity of the radiolabeled groups of the compounds of the present invention.

It is possible for the Radiolabeled Compounds of the present invention to have one or more chiral centers, and, as such, the Radiolabeled Compounds can exist in various stereoisomeric forms. Accordingly, Formula (I) and Formula (II), although not depicting specific stereoisomers of the Radiolabeled Compounds, are understood to encompass all possible stereoisomers.

The Radiolabeled Compounds of Formula (I)

As stated above, the present invention encompasses Radiolabeled Compounds having the formula (I):

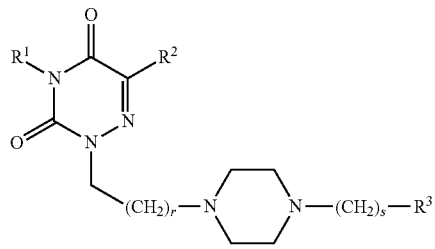

or pharmaceutically acceptable salts thereof, wherein $R^1$, $R^2$ and $R^3$ are as defined above for the Radiolabeled Compounds of Formula (I).

In one embodiment, $R^1$ is $C_1$-$C_6$ alkyl.

In another embodiment, $R^1$ is methyl.

In one embodiment, $R^2$ is H.

In another embodiment, $R^2$ is H, and $R^1$ is methyl.

In one embodiment, $R^3$ is aryl.

In another embodiment, $R^3$ is naphthyl.

In still another embodiment, $R^3$ is naphthyl substituted with —$O^{11}CH_3$.

In one embodiment, r is 3.

In another embodiment, s is 0.

In still another embodiment, r is 3 and s is 0.

In yet another embodiment, $R^3$ is naphthyl substituted with —$O^{11}CH_3$, r is 3, and s is 0.

Illustrative Radiolabeled Compounds of Formula (I)) include the compounds having the structure:

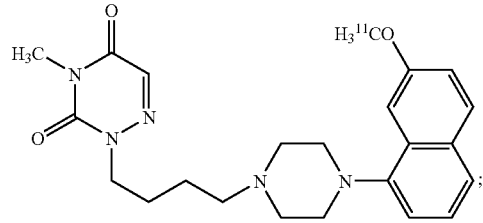

A

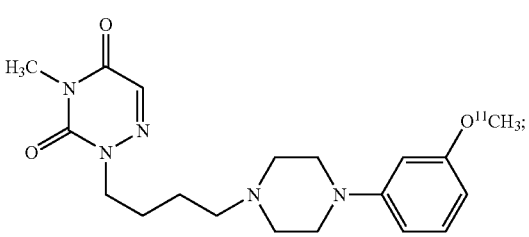

B

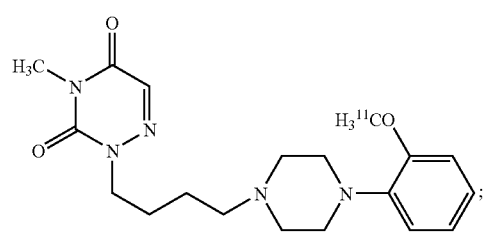

C

-continued

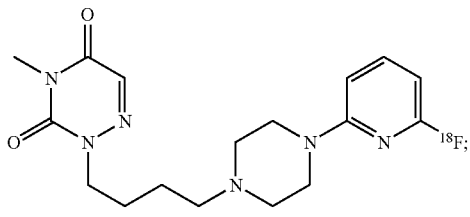

and pharmaceutically acceptable salts thereof.

The Radiolabeled Compounds of Formula (I) can act as agonists or antagonists of the 5-$HT_{1A}$ receptor.

In one embodiment, a Radiolabeled Compound of Formula (I) is an antagonist of the 5-$HT_{1A}$ receptor.

In another embodiment, a Radiolabeled Compound of Formula (I) is an agonist of the 5-$HT_{1A}$ receptor.

The Radiolabeled Compounds of Formula (II)

As stated above, the present invention encompasses Radiolabeled Compounds having the formula (II):

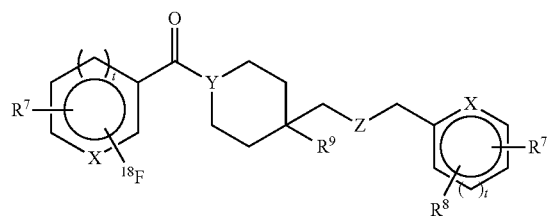

or pharmaceutically acceptable salts thereof, wherein X, Y, Z, $R^7$, $R^8$, $R^9$ and t are as defined above for the Radiolabeled Compounds of Formula (II).

In one embodiments, each $R^7$ is independently —H, —F, —Cl, a straight or branched chain saturated aliphatic hydrocarbon radical containing 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl, or 2-ethyl-propyl; a fluoroalkyl radical such as fluoromethyl, difluoromethyl, trifluoromethyl, —CH(F)$CH_3$ or —$CF_2CH_3$; a cyclopropyl, cyclobutyl, or cyclopentyl radical; a substituted or unsubstituted 5-membered aromatic heterocyclic group containing 1 to 3 heteroatoms selected from nitrogen, oxygen, and sulfur, such that the heterocycle cannot have more than one sulfur ring atom and one oxygen ring atom; —$OR^{10}$ or —$SR^{10}$ where $R^{10}$ is independently a straight or branched chain saturated aliphatic hydrocarbon radical containing 1 to 5 carbon atoms, a monofluoromethyl or trifluoromethyl radical, a cyclopropyl radical, a cyclobutyl radical, or a cyclopentyl radical; or an alkoxycarbonyl group such as —OC(O)$CH_3$ or —OC(O)—$CH_2CH_3$.

In another embodiments, $R^8$ is —$Z^a$—$R^{12}$, —H, —F, —Cl, a straight or branched chain saturated aliphatic hydrocarbon radical containing 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl, or 2-ethyl-propyl; a fluoroalkyl radical such as fluoromethyl, difluoromethyl, trifluoromethyl, —CH(F)$CH_3$ or —$CF_2CH_3$; a cyclopropyl, cyclobutyl, or cyclopentyl radical; a substituted or unsubstituted 5-membered aromatic heterocyclic group containing 1 to 3 heteroatoms selected from nitrogen, oxygen, and sulfur, such that the heterocycle cannot have more than one sulfur ring atom and one oxygen ring atom; —$OR^{10}$ or —$SR^{10}$ where $R^{10}$ is independently a straight or branched chain saturated aliphatic hydrocarbon radical containing 1 to 5 carbon atoms, a monofluoromethyl or trifluoromethyl radical, a cyclopropyl radical, a cyclobutyl radical, or a cyclopentyl radical; or an alkoxycarbonyl group such as OC(O)$CH_3$ or —OC(O)—$CH_2CH_3$.

In still another embodiment, $R^{12}$ is —$^{11}$C-labeled $C_1$-$C_6$ alkyl, —$^{11}$C-labeled $C_2$-$C_6$ alkenyl, —$^{11}$C-labeled $C_2$-$C_6$ alkynyl, —($^{11}$C-labeled $C_1$-$C_6$ alkylene)-aryl, —($^{11}$C-labeled $C_2$-$C_6$ alkenylene)-aryl, or —($^{11}$C-labeled $C_2$-$C_6$ alkynylene)-aryl.

In a further embodiment, $Z^a$ is —O—, —S—, or —NH—.

In another embodiment, $R^9$ is —H or —F.

In still another embodiment X is —N—.

In yet another embodiment Y is —N—.

In a further embodiment Z is —NH—.

In another embodiment t is 1.

Illustrative Radiolabeled Compounds of Formula (II) include the compounds having the structure:

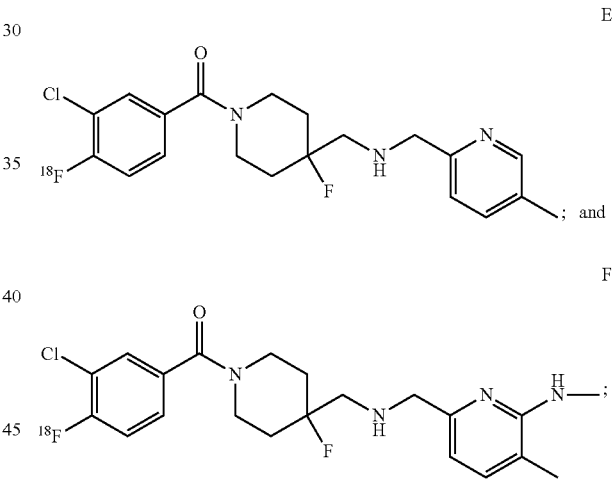

and pharmaceutically acceptable salts thereof.

The Radiolabeled Compounds of Formula (II) can act as agonists or antagonists of the 5-$HT_{1A}$ receptor.

In one embodiment, a Radiolabeled Compound of Formula (II) is an antagonist of the 5-$HT_{1A}$ receptor.

In another embodiment, a Radiolabeled Compound of Formula (II) is an agonist of the 5-$HT_{1A}$ receptor.

Methods for Making the Radiolabeled Compounds of Formula (I)

The Radiolabeled Compounds of Formula (I) can be made using the synthetic procedures outlined below in Schemes 1-3.

Scheme 1 shows methods for making the Radiolabeled Compounds of Formula (I).

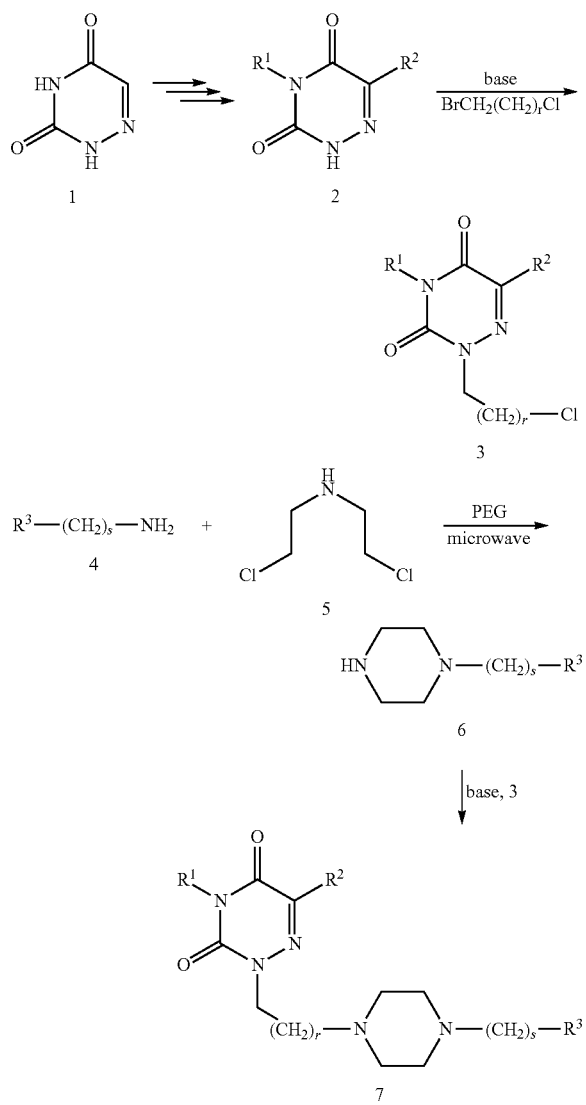

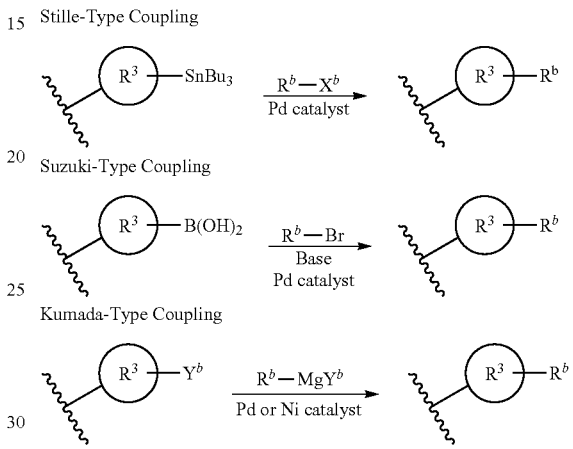

Scheme 2 shows methods for attaching the following radiolabeled groups to the $R^3$ group of a precursor to a Radiolabeled Compound of Formula (I): $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl.

wherein r, s, $R^1$, $R^2$ and $R^3$ are defined above for the Compounds of Formula (I).

The heterocyclic compound 1 can be used as is or can be derivatized using methods well-known to one of ordinary skill in the art of organic synthesis to prepare compounds of formula 2 wherein one or both of $R^1$ and $R^2$ are other than hydrogen. The compounds of Formula 2 are then alkylated using an alkylating agent of Formula BrCH$_2$(CH$_2$)$_r$Cl in the presence of a base to provide the synthetic intermediates of Formula 3.

An amine of Formula 4 can be reacted with di-(2-chloroethyl)amine using microwave irradiation to provide the piperazine intermediates of formula 6. Finally, a compound of Formula 6 is coupled with a compound of Formula 3 in the presence of a base to provide the Compounds of Formula 7.

It will be apparent to one of ordinary skill in the art that radiolabeled group $R^6$, which is a substituent on group $R^3$ in the compounds of Formula (I) may be present in the compounds of Formula 4 or alternatively may be absent from the compounds of Formula 4. In the latter case, the radiolabeled group $R^6$ may be attached to group $R^3$ in any step of the synthesis, or alternatively, may be attached to an intact compound of Formula 7.

wherein $R^3$ is defined above for the Radiolabeled Compounds of Formula (I); $X^b$ is Cl, Br, I, or OTf; Ra is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl; and each occurrence of $Y^b$ is independently Cl, Br, or I.

An $R^3$ group of a precursor to a Radiolabeled Piperazine Compound of formula (I) can be substituted with a radiolabeled group at any point during the synthetic route outlined in Scheme 1. As outlined in Scheme 2, the unlabeled $R^3$ group of a Compound of formula 4, 6 or 7 as shown in Scheme 1 can be subjected to a palladium- or nickel-catalyzed coupling process including, but not limited to a Suzuki coupling (A. Suzuki, Pure Appl. Chem. 1991, 63:419-422), a Kumada coupling (M. Kumada, Pure Appl. Chem. 1980, 52:669), or a Stille coupling (J. K. Stille, Angew. Chem. Int. Ed. 1986, 25:508-524) process to provide a product which contains an $R^3$ group that is substituted with any of the following radiolabeled groups: —$^{11}$C-labeled $C_1$-$C_6$ alkyl, —$^{11}$C-labeled $C_2$-$C_6$ alkenyl, —$^{11}$C-labeled $C_2$-$C_6$ alkynyl, —($^{11}$C-labeled $C_1$-$C_6$ alkylene)-aryl, —($^{11}$C-labeled $C_2$-$C_6$ alkenylene)-aryl, —($^{11}$C-labeled $C_2$-$C_6$ alkynylene)-aryl, —$^{18}$F-labeled $C_1$-$C_6$ alkyl, —$^{18}$F-labeled $C_2$-$C_6$ alkenyl, —$^{18}$F-labeled $C_2$-$C_6$ alkynyl, —($^{18}$F-labeled $C_1$-$C_6$ alkylene)-aryl, —($^{18}$F-labeled $C_2$-$C_6$ alkenylene)-aryl, or —($^{18}$F-labeled $C_2$-$C_6$ alkynylene)-aryl.

Scheme 3 shows methods for attaching radiolabeled groups of formula $Z^c$—$R^c$ to an $R^3$ group of a precursor to a Radiolabeled Compound of Formula (I), wherein $Z^c$ is O, S, or NH; and $R^c$ is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled C$_2$-C$_6$ alkenylene)-aryl, ($^{11}$C-labeled C$_2$-C$_6$ alkynylene)-aryl, $^{18}$F-labeled C$_1$-C$_6$ alkyl, $^{18}$F-labeled C$_2$-C$_6$ alkenyl, $^{18}$F-labeled C$_2$-C$_6$ alkynyl, ($^{18}$F-labeled C$_1$-C$_6$ alkylene)-aryl, ($^{18}$F-labeled C$_2$-C$_6$ alkenylene)-aryl, or ($^{18}$F-labeled C$_2$-C$_6$ alkynylene)-aryl.

Scheme 3

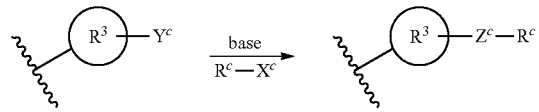

wherein R$^3$ is defined above for the Radiolabeled Compounds of Formula (I); R$^c$ is $^{11}$C-labeled C$_1$-C$_6$ alkyl, $^{11}$C-labeled C$_2$-C$_6$ alkenyl, $^{11}$C-labeled C$_2$-C$_6$ alkynyl, ($^{11}$C-labeled C$_1$-C$_6$ alkylene)-aryl, ($^{11}$C-labeled C$_2$-C$_6$ alkenylene)-aryl, ($^{11}$C-labeled C$_2$-C$_6$ alkynylene)-aryl,), $^{18}$F-labeled C$_1$-C$_6$ alkyl, $^{18}$F-labeled C$_2$-C$_6$ alkenyl, $^{18}$F-labeled C$_2$-C$_6$ alkynyl, ($^{18}$F-labeled C$_1$-C$_6$ alkylene)-aryl, ($^{18}$F-labeled C$_2$-C$_6$ alkenylene)-aryl, or ($^{18}$F-labeled C$_2$-C$_6$ alkynylene)-aryl; X$^c$ is Cl, Br, I, OMs, OTs, or OTf; Y$^c$ is OH, SH, or NH$_2$; and Z$^c$ is O, S, or NH.

An OH, NH$_2$, or SH group attached to an R$^3$ group of a compound of Formula 4, 6 or 7 as shown in Scheme 1 can be treated with base and the resulting oxygen, sulfur, or nitrogen anion can be reacted with a group having the formula R$^c$—X$^c$, wherein X$^c$ is Cl, Br, I, OMs, OTs, or OTf, to provide a product which contains an R$^3$ group that is substituted with a radiolabeled group of formula Z$^c$—R$^c$, wherein Z$^c$ is O, S, or NH; and R$^c$ is $^{11}$C-labeled C$_1$-C$_6$ alkyl, $^{11}$C-labeled C$_2$-C$_6$ alkenyl, $^{11}$C-labeled C$_2$-C$_6$ alkynyl, ($^{11}$C-labeled C$_1$-C$_6$ alkylene)-aryl, ($^{11}$C-labeled C$_2$-C$_6$ alkenylene)-aryl, ($^{11}$C-labeled C$_2$-C$_6$ alkynylene)-aryl, $^{18}$F-labeled C$_1$-C$_6$ alkyl, $^{18}$F-labeled C$_2$-C$_6$ alkenyl, $^{18}$F-labeled C$_2$-C$_6$ alkynyl, ($^{18}$F-labeled C$_1$-C$_6$ alkylene)-aryl, ($^{18}$F-labeled C$_2$-C$_6$ alkenylene)-aryl, or ($^{18}$F-labeled C$_2$-C$_6$ alkynylene)-aryl.

Radiolabeled compounds of Formula (I) that can be made using the methods of the invention include the compound having the Formula (A), (B), and pharmaceutically acceptable salts thereof.

Methods for Making the Radiolabeled Compounds of Formula (II)

The Radiolabeled Compounds of Formula (II) can be made using the synthetic procedures outlined in Scheme 4 below.

Scheme 4

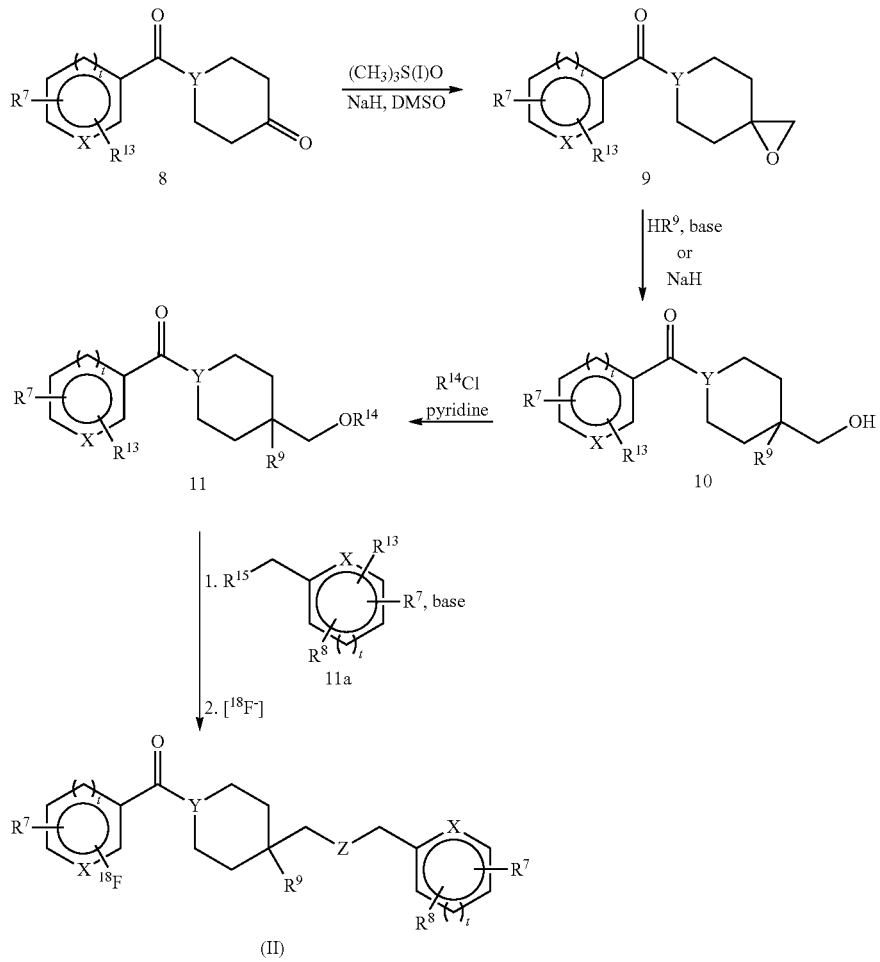

wherein $R^7$, $R^8$, $R^9$, X, Y, Z, and t are defined above for the Radiolabeled Compounds of Formula (II); $R^{13}$ is —F or —$NO_2$; $R^{14}$ is -mesyl, -tosyl or -triflyl; and $R^{15}$ is —OH, —SH, or —$NH_2$.

A compound of Formula 8 can be reacted with trimethylsulfoxonium iodide in the presence of NaH to provide an epoxide compound of formula 9. The epoxide ring of Formula 9 can then be reacted with: (1) a compound of formula $HR^9$ in the presence of a base, where $R^9$ is -halo to provide a compound of Formula 10 wherein $R^9$ is -halo; or (2) NaH to provide a compound of Formula 10 wherein $R^9$ is —H. The hydroxyl group of a compound of Formula 10 can be converted to a leaving group by reacting with a compound of formula $R^{14}Cl$ in the presence of a non-nucleophilic base, such as pyridine to provide a compound of Formula 11. Finally, a compound of Formula 11 can be coupled with a compound of Formula 11a in the presence of base and the resultant adduct can then be reacted with Kryptofix 222/[$^{18}$F] and potassium carbonate as described in de Vries et al., *Journal of Nuclear Medicine* 2003, 44:1700-1706, to provide the Radiolabeled Compounds of Formula (II).

Uses of the Radiolabeled Compounds as Radiological Imaging Agents

The Radiolabeled Compounds can be used as imaging agents to image one or more 5-$HT_{1A}$ receptors in a subject.

In one embodiment, the present invention relates to the use of a Radiolabeled Compound for detecting one or more 5-$HT_{1A}$ receptors in vivo. In particular, the present methods for detecting 5-$HT_{1A}$ receptors in vivo contemplate the use of PET, where the imaging probe is a Radiolabeled Compound of the present invention.

In another embodiment, the invention provides a method for imaging one or more 5-$HT_{1A}$ receptors in a subject comprising the steps: (a) administering to the subject an imaging-effective amount of a Radiolabeled Compound or pharmaceutically acceptable salt thereof, and (b) detecting the radioactive emission of the compound or salt thereof administered in step (a).

In one embodiment, the detecting of step (b) is carried out using PET.

In another embodiment, the 5-$HT_{1A}$ receptors being imaged are in the brain of the subject.

Methods for imaging, and thereby detecting, 5-$HT_{1A}$ receptors in vivo are desirable in order to screen individuals for psychiatric neurological disorders or for diseases, disorders, states or conditions that are related to the binding of serotonin to 5-$HT_{1A}$ receptors. For example, the following list of processes, diseases or disorders may involve alterations in normal binding of serotonin to 5-$HT_{1A}$ receptors: mood disorders, such as a major depressive disorder or bipolar disorder; an eating disorder, such as anorexia nervosa or bulimia; an addictive disorder, such as drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; a seizure disorder, such as temporal lobe epilepsy. Further, Radiolabeled Compounds of the present invention which are selective for the 5-$HT_{1A}$ receptor can be used to screen for individuals who are more likely to respond to drugs that act on these receptors or susceptible to side effects of drugs which bind to the 5-$HT_{1A}$ receptor, as manifested by an increased detection of radiolabeled 5-$HT_{1A}$ selective agents in specified tissue compartments. These compounds can used to identify the dose range of drugs to treat illnesses and disorders that work by binding to this receptor.

In one embodiment, the Radiolabeled Compounds have high specific activity. In one embodiment, the invention provides Radiolabeled Compounds having a specific activity that is greater than about 1000 Ci/micromole.

Further, the Radiolabeled Compounds may have a high affinity and specificity to the 5-$HT_{1A}$ receptor. In one embodiment, the Radiolabeled Compounds have a 5-$HT_{1A}$ receptor binding affinity that is from about 20 to about 100,000 greater than the binding affinity for any of the other known transporters, receptors, enzymes, and peptides.

The Radiolabeled Compounds of the present invention can be used to detect and/or quantitatively measure 5-$HT_{1A}$ receptor levels in subjects, including humans. The Radiolabeled Compounds of the present invention can also be used to measure and/or detect 5-$HT_{1A}$ receptors in 5-$HT_{1A}$ receptor related diseases, conditions and disorders, including but not limited to, mood disorders, such as a major depressive disorder or bipolar disorder; an eating disorder, such as anorexia nervosa or bulemia; an addictive disorder, such as drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; a seizure disorder, such as temporal lobe epilepsy.

The ability to quantitatively measure 5-$HT_{1A}$ receptor levels in a subject is useful for pre-screening subjects and in one embodiment, a Radiolabeled Compound of the present invention can be administered to a subject to help determine whether the subject is likely to be a responder or non-responder to medicinal agents which bind 5-$HT_{1A}$ receptors. The ability to quantitatively measure 5-$HT_{1A}$ receptor levels in a subject is useful for pre-screening clinical trial patient populations.

The Radiolabeled Compounds of the present invention can be used to detect or monitor processes, diseases or disorders that may involve the binding of serotonin to 5-$HT_{1A}$ receptors, including but not limited to, a mood disorder, such as a major depressive disorder or bipolar disorder; an eating disorder, such as anorexia nervosa or bulimia; an addictive disorder, such as drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; a psychotic disorder, such as schizophrenia; a movement disorder, such as Parkinson's disease; an anxiety disorder such as panic disorder, or obsessive-compulsive disorder or social phobia; a seizure disorder, such as temporal lobe epilepsy.

The Radiolabeled Compounds of the present invention can also be used to help determine the capacity that one or more 5-$HT_{1A}$ receptors have for signaling. In this embodiment, the present methods for imaging 5-$HT_{1A}$ receptors can be used to determine the percentage of 5-$HT_{1A}$ receptors that are at high affinity state. In a specific embodiment, the Radiolabeled Compound of the present invention being administered for imaging one or more 5-$HT_{1A}$ receptors, is an agonist of the 5-$HT_{1A}$ receptor.

Further, the Radiolabeled Compounds of the present invention can be used to screen for individuals who are more susceptible to side effects of agents which bind to 5-HT$_{1A}$ receptors, as manifested by an increased detection of the Radiolabeled Compounds of the present invention in specified tissue compartments.

Additionally, the Radiolabeled Compounds of the present invention are useful in drug discovery programs and in one embodiment, can be used to determine the efficacy of agents that bind to 5-HT$_{1A}$ receptors when such agents are administered to a subject to treat a disorder whose etiology involves the binding of serotonin to one or more 5-HT$_{1A}$ receptors. In another embodiment, the Radiolabeled Compounds of the present invention can be used to monitor the occupancy rate of 5-HT$_{1A}$ receptors in a subject after the subject has been administered an agent which binds to 5-HT$_{1A}$ receptors. In one embodiment, the occupancy rate of 5-HT$_{1A}$ receptors for experimental drugs can be used to help determine optimal dosage levels of such drugs. In so far as the Radiolabeled Compound of the present invention is an agonist, it has special advantages in quantifying the receptor occupancy of potential new therapeutic agents that are also agonists and therefore in determining the optimal dose to use for those agents as part of an Investigational New Drug (IND) application process and thereby shorten the time period to acquire data for regulatory approval for marketing and general use in treatment. When the Radiolabeled Compound of the present invention is an agonist it will also aid the study and diagnosis of disease by being more sensitive to the quantification of serotonin release and depletion.

Alternatively, the methods for detection can be used to monitor the course of a 5-HT$_{1A}$ receptor related disease in an individual. Thus, whether a particular therapeutic regimen aimed at ameliorating the cause of the disease, or the disease process itself, is effective, can be determined by measuring the decrease of 5-HT$_{1A}$ receptors at suspected sites of disease.

In a further embodiment, the present methods for imaging one or more 5-HT$_{1A}$ receptors can provide images of the location of 5-HT$_{1A}$ receptors and serve as a guide to surgeons who are operating in the area of such receptors. In one embodiment, the surgeon is a neurosurgeon operating on the brain of a subject.

Uses of the Radiolabeled Compounds to Treat or Prevent a Psychiatric Disorder A psychiatric disorder can be treated or prevented by administration of a therapeutically effective amount of a Radiolabeled Compound of the present invention.

Psychiatric disorders that can be treated or prevented by administering a therapeutically effective amount of a Radiolabeled Compound of the present invention include, but are not limited to, a mood disorder, such as a major depressive disorder, bipolar disorder, manic depression, depression, cyclothymia, dysthymia, or borderline personality disorder; an eating disorder, such as anorexia nervosa or bulemia; an addictive disorder, such as drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; a seizure disorder, such as temporal lobe epilepsy.

In one embodiment, the psychiatric disorder is a mood disorder.

In another embodiment, the psychiatric disorder is an eating disorder.

In another embodiment, the psychiatric disorder is an addictive disorder.

In another embodiment, the psychiatric disorder is a disease associated with cognitive dysfunction.

In a specific embodiment, the psychiatric disorder is Alzheimer's disease.

In still another embodiment, the psychiatric disorder is a neurodegenerative disease.

In yet another embodiment, the psychiatric disorder is a pain disorder.

In another embodiment, the psychiatric disorder is a psychotic disorder.

In one embodiment, the psychiatric disorder is a movement disorder.

In another embodiment, the psychiatric disorder is an anxiety disorder.

In still another embodiment, the psychiatric disorder is a seizure disorder.

In yet another embodiment, the psychiatric disorder is an obsessive-compulsive disorder.

Uses of the Radiolabeled Compounds to Stabilize the Mood of a Subject Having a Mood Disorder The mood of a subject having a mood disorder can be stabilized by administration of a therapeutically effective amount of a Radiolabeled Compound of the present invention.

Mood disorders in which the Radiolabeled Compounds of the present invention are useful for stabilizing the mood include, but are not limited to, a major depressive disorder, bipolar disorder, manic depression, depression, cyclothymia, dysthymia, and borderline personality disorder.

In one embodiment, the mood disorder is a major depressive disorder.

In another embodiment, the mood disorder is bipolar disorder.

Examples of conditions treatable or preventable using the Radiolabeled Compounds of the present invention include, but are not limited to, an eating disorder, such as anorexia nervosa or bulemia; drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; or a seizure disorder, such as temporal lobe epilepsy.

Therapeutic/Diagnostic Administration of the Radiolabeled Compounds

The Radiolabeled Compounds of the present invention are advantageously useful in veterinary and human medicine. As described above, the Radiolabeled Compounds of the present invention are useful for imaging 5-HT$_{1A}$ receptors in a subject.

When administered to a subject, the Radiolabeled Compounds of the present invention can be administered as a component of a composition that comprises a physiologically acceptable carrier or vehicle. The present compositions, which comprise a Radiolabeled Compound of the present invention, can be administered orally or by any other convenient route, for example, by infusion or bolus injection, or by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be administered.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result in the release of the Radiolabeled Compounds of the present invention into the bloodstream. The mode of administration is left to the discretion of the practitioner.

In one embodiment, the Radiolabeled Compounds of the present invention are administered orally.

In another embodiment, the Radiolabeled Compounds of the present invention are administered intravenously.

In another embodiment, the Radiolabeled Compounds of the present invention are administered transdermally.

In other embodiments, it can be desirable to administer the Radiolabeled Compounds of the present invention locally. This can be achieved, for example, and not by way of limitation, by local infusion during surgery, by injection, by means of a catheter, by means of a suppository or enema, or by means of an implant, said implant being of a porous, nonporous, or gelatinous material, including membranes, such as sialastic membranes, or fibers.

In certain embodiments, it can be desirable to introduce the Radiolabeled Compounds of the present invention into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon or a synthetic pulmonary surfactant.

In another embodiment the Radiolabeled Compounds of the present invention can be delivered in a vesicle, in particular a liposome (see Langer, *Science* 249:1527-1533 (1990) and *Liposomes in the Therapy of Infectious Disease and Cancer*, pp. 317-327 and 353-365 (1989)).

In yet another embodiment the Radiolabeled Compounds of the present invention can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

The present compositions can optionally comprise a suitable amount of a physiologically acceptable excipient so as to provide the form for proper administration of a Radiolabeled Compound of the present invention to the subject.

Such physiologically acceptable excipients can be liquids, such as water for injection, bactereostatic water for injection, sterile water for injection, and oils, including those of petroleum, subject, vegetable, or synthetic origin, such as peanut oil, soybean oil, mineral oil, sesame oil and the like. The pharmaceutical excipients can be saline, gum acacia; gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to a subject. Water is a particularly useful excipient when the Radiolabeled Compound of the present invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills; pellets, capsules, capsules containing liquids, powders, sustained-release formulations, suppositories, emulsions. aerosols, sprays, suspensions, or any other form suitable for use. In one embodiment the composition is in the form of a capsule (see e.g. U.S. Pat. No. 5,698,155). Other examples of suitable physiologically acceptable excipients are described in *Remington's Pharmaceutical Sciences* 1447-1676 (Alfonso R. Gennaro eds., 19th ed. 1995), incorporated herein by reference.

In one embodiment the Radiolabeled Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In one embodiment, when a Radiolabeled Compound is orally administered, the Radiolabeled Compound is administered in combination with an additional therapeutic agent that can increase the oral bioavailability of the Radiolabeled Compound, as described, for example, in U.S. Pat. No. 6,008, 222. The additional therapeutic agent may be administered separately from the Radiolabeled Compound or the additional agent and the Radiolabeled Compound may be co-administered as part of the same composition. In a specific embodiment, the additional agent that increases the oral bioavailability of a Radiolabeled Compound is nefazodone.

In another embodiment the Radiolabeled Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the Radiolabeled Compounds are to be administered by infusion, they can be dispensed, for example, with an infusion bottle containing sterile pharmaceutical grade water or saline. Where the Radiolabeled Compounds are administered by injection, an ampule of sterile water for injection or saline can be provided so that the ingredients can be mixed prior to administration.

The Radiolabeled Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,431,922; 5,354,556; and 5,733,556, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the Radiolabeled Compounds of the invention. The invention thus encompasses single unit dosage forms suitable for oral administration such as, but not limited to, tablets, capsules, gelcaps, and caplets that are adapted for controlled- or sustained-release. The invention also encompasses transdermal delivery devices, including but not limited to, a transdermal patch and other devices, such as those described in U.S. Pat. No. 5,633,009.

In one embodiment a controlled- or sustained-release composition comprises a minimal amount of a Radiolabeled Compound to image one or more 5-HT$_{1A}$ receptors in a subject. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Radiolabeled Compound, and can thus reduce the occurrence of adverse side effects.

Controlled- or sustained-release compositions can initially release an amount of a Radiolabeled Compound that promptly produces the desired diagnostic effect, and gradually and continually release other amounts of the Radiolabeled Compound to maintain this level of diagnostic effect over an extended period of time. To maintain a constant level of the Radiolabeled Compound in the body, the Radiolabeled Compound can be released from the dosage form at a rate that will replace the amount of Radiolabeled Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions.

The amount of the Radiolabeled Compound that is effective as an imaging agent to detect one or more 5-HT$_{1A}$ receptors in a subject can be determined using standard clinical and nuclear medicine techniques. In addition, in vitro or in vivo testing can optionally be employed to help identify optimal dosage ranges. The precise dose to be employed will also depend on certain factors—the route of administration, the identity of the subject and the identity of the particular radionuclide being detected—and should be decided according to the judgment of the practitioner and each subject's circumstances in view of, e.g., published clinical studies. Suitable imaging-effective dosage amounts, however, range from about about 0.01 mCi to about 30 mCi; about 2 mCi to about 30 mCi; about 10 to about 30 mCi or preferably from about 2 mCi to about 5 mCi. The Radiolabeled Compounds will have a specific activity of >1000 Ci/micromol at the time of administration to insure a low injected mass and adequate counts for imaging. The imaging-effective dosage amounts described herein refer to total amounts administered; that is, if more than one dose of a Radiolabeled Compound is administered, the imaging-effective dosage amounts correspond to the total amount administered.

Kits

The invention encompasses kits that can simplify the administration of a Radiolabeled Compound to a subject.

A typical kit of the invention comprises a unit dosage form of a Radiolabeled Compound.

In one embodiment the unit dosage form is within a container, which can be sterile, containing a therapeutically effective amount of a Radiolabeled Compound and a physiologically acceptable carrier or vehicle. The kit can further comprise a label or printed instructions instructing the use of the Radiolabeled Compound to (i) treat or prevent a psychiatric disorder in a subject, or (ii) stabilize the mood of a subject having a mood disorder.

In another embodiment the unit dosage form is within a container, which can be sterile, containing an imaging-effective amount of a Radiolabeled Compound and a physiologically acceptable carrier or vehicle. The kit can further comprise a label or printed instructions instructing the use of the Radiolabeled Compound as an imaging agent in order to image or detect one or more 5-HT$_{1A}$ receptors in a subject.

Kits of the invention can further comprise a device that is useful for administering the unit dosage forms. Examples of such a device include, but are not limited to, a syringe, a drip bag, a patch, an inhaler, and an enema bag.

EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

General Methods

Proton nuclear magnetic resonance (NMR) spectra were obtained from Bruker PPX 300 and 400 MHz spectrophotometer. Spectra are recorded in CDCl$_3$ and the chemical shifts are reported in parts per million relative to TMS for $^1$H NMR as internal standards. The mass spectra were recorded on JKS-HX 11UHF/HX110 HF Tandem Mass Spectrometer in the FAB+ mode. Flash column chromatography was performed on silica gel (Fisher 200-400 mesh) using the solvent system indicated. The radiochemical and chemical purities were analyzed by RP-HPLC with PDA and NaI detectors.

Example 1

Preparation of Compound A

Step A: Preparation of Intermediate Compound 15

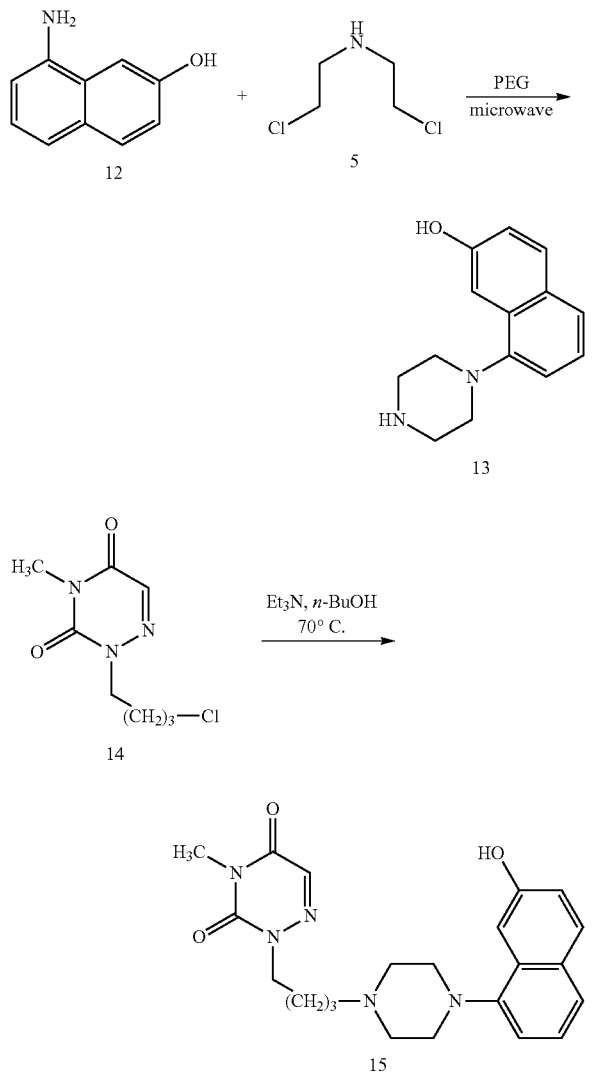

Amine 12 (796 mg, 5 mmol) was diluted with PEG-400 (2 mL) and to the resulting solution was added dichloroamine compound 5 (892 mg, 5 mmol). The resulting reaction was heated under microwave conditions for 10 seconds, then allowed to cool to room temperature. This heat/cool process was repeated two more times. It is noted that during the heating/cooling cycles, copious amounts of hydrochloric acid gas is released. After the evolution of hydrochloric acid gas subsided, the reaction mixture was triturated using chloroform to precipitate out a crude solid residue. The crude solid residue was filtered and washed with chloroform. The washed solid was then recrystallized from chloroform:methanol to provide compound 13 in 54% yield. $^1$H NMR (CDCl$_3$, 400 MHz) δ 7.80 (d, J=11.6 Hz, 1H), 7.62 (d, J=8.1 Hz, 1H), 7.53-7.54 (m, 1H), 7.30 (m, 1H), 7.22 (s, 1H), 7.15-7.20 (m, 1H), 3.60 (t, J=6.8 Hz, 4H), 3.39-3.41 (m, 4H).

Piperazine compound 13 (272 mg, 1.19 mmol) was diluted with n-butanol (4 mL) and to the resulting solution was added chloride compound 14 (151 mg, 0.7 mmol, commercially available), followed by dropwise addition of triethylamine (0.5 mL). The resulting reaction was heated at reflux for about 12 hours, allowed to cool to room temperature, then concentrated in vacuo to provide a crude residue. The crude residue was triturated with diethyl ether and the resultant off-white solid which precipitated out was filtered, washed with diethyl ether (50 mL), then purified using flash column chromatography on silica gel (mobile phase-gradient of 5% to 10% methanol in chloroform) to provide precursor compound 15 as a colorless solid (146 mg, 51%). M.p=205-206° C. $^1$H NMR (400 MHz, CDCl$_3$): δ 7.71 (d, 11.7 Hz, 1H), 7.48-7.45 (m, 2H), 7.37 (s, 1H), 7.22-7.19 (m, 1H), 7.08-7.4 (m, 2H), 4.02 (t, J=9.5 Hz, 2H), 3.33 (s, 3H), 3.19-3.08 (m, 4H), 2.85-2.70 (m, 4H), 2.54-2.49 (t, J=10.1 Hz, 2H), 1.87-1.77 (m, 2H), 1.66-1.56 (m, 2H). HRMS calcd for C$_{22}$H$_{28}$O$_3$N$_5$ (MH$^+$): 410.2192. Found: 410.2194.

Step B: Radiolabeling of Compound 15 to Provide Compound A:

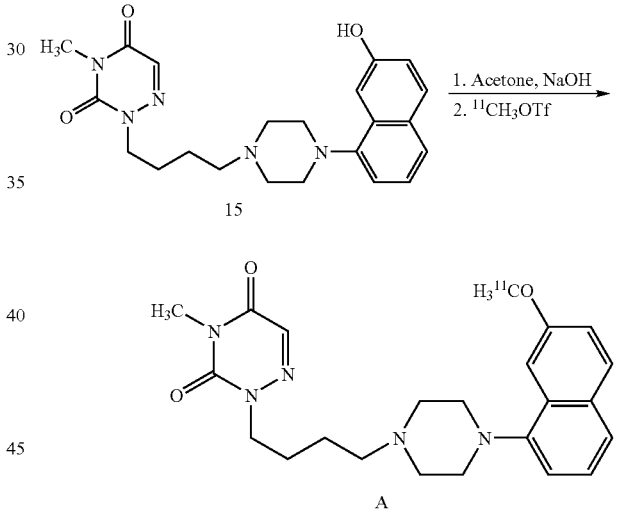

Precursor compound 15 (1.0 mg) was placed in a 1 mL vial. To the vial was added acetone (400 μL), followed by 5 M sodium hydroxide (10 μL). The resulting solution was allowed to stand for 5 minutes, then [$^{11}$C]-methyl triflate was transported by a stream of argon (20-30 mL/min) into the vial over a period of 5 minutes at room temperature. The reaction mixture was removed from the vial via syringe and directly injected onto a semi preparative RP-HPLC column (Phenomenex C18, 10 mm×250 mm) and eluted at a flow rate of 10 mL/min using a mobile phase of acetonitrile:0.1 M aqueous ammonium formate (40:60). Compound A eluted at 8-9 minutes and the fractions containing Compound A were collected, diluted with deionized water (100 μL added to each fraction), and combined. The combined diluted fractions were filtered through a C-18 Sep-Pak cartridge and concentrated in vacuo to provide a crude residue which was reconstituted using absolute ethanol (1 mL) to provide Compound A (35% yield based on [$^{11}$C]CO$_2$ at EOS).

Example 2

Preparation of Compound B

Step A: Preparation of Intermediate Compound 17

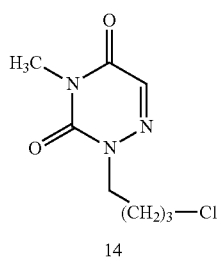
14

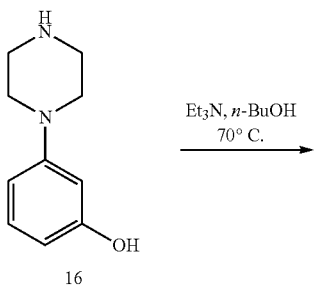
16

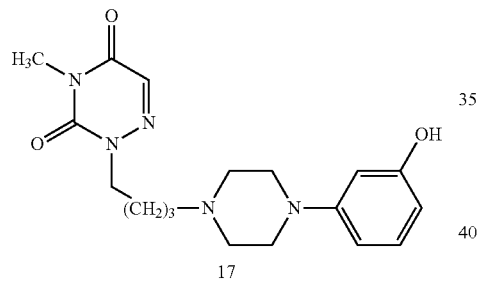
17

Piperazine compound 16 (150 mg, 0.84 mmol, commercially available) and chloride compound 14 (183 mg, 0.84 mmol, commercially available) were diluted with n-butanol (5 mL) and to the resulting solution was added triethylamine (0.5 mL, added drop wise). The resulting reaction was heated and refluxed for about 12 hours, allowed to cool to room temperature, then concentrated in vacuo to provide a crude residue. The crude residue was triturated using diethyl ether and the resultant off-white precipitate was filtered, washed with diethyl ether (50 mL) and purified using flash column chromatography on silica gel (mobile phase was gradient of 5% to 10% methanol in dichloromethane) to provide precursor compound 17 as a colorless solid (220 mg, 73%). m.p=162-64° C., $^1$H NMR (300 MHz, CDCl$_3$): δ 7.35 (s, 1H), 7.0 (m, 1H), 6.4 (d, 1H, J=8.16), 6.2-6.3 (2H, m), 4.0 (t, J=7 Hz, 2H), 3.3 (s, 3H), 3.14-3.15 (m, 4H), 2.5-2.6 (m, 4H), 2.4 (t, J=7 Hz, 2H), 1.7 (m, 2H), 1.5 (m, 2H). HRMS calcd for C$_{18}$H$_{26}$O$_3$N$_5$ (MH$^+$): 360.2036. Found: 360.2033.

Step B: Radiolabeling of Compound 17 to Provide Compound B:

Compound B was made using the method described in Example 1, Step B, substituting Compound 17 for Compound 15.

Example 3

Preparation of Compound C

Step A: Preparation of Intermediate Compound 19

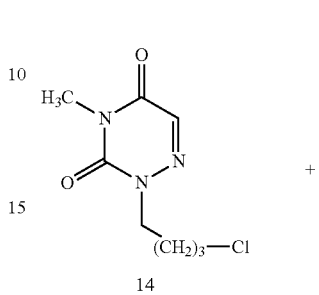
14

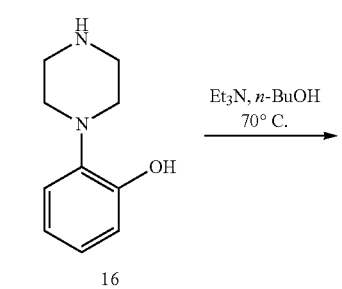
16

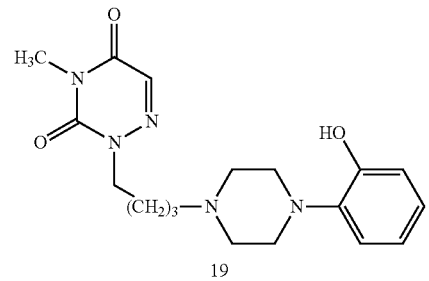
19

Intermediate compound 19 was made using the method described in Example 1, Step A, and substituting Compound 18 for Compound 13. Compound 18 can be made using the method set forth in Example 5.1, Step A, and substituting 8-amino-1-naphthol for Compound 12.

Step B: Radiolabeling of Compound 19 to Provide Compound C:

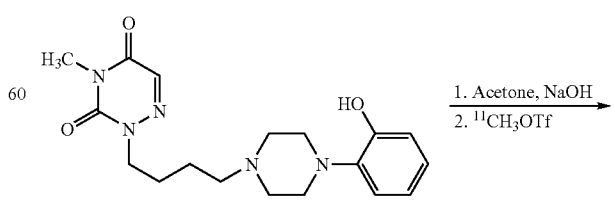
19

-continued

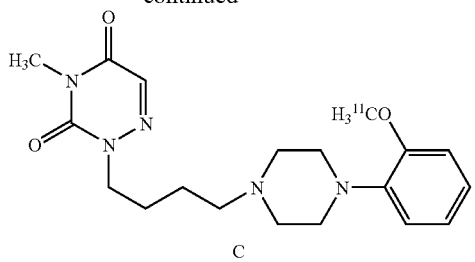

C

Compound C was made using the method described in Example 5.1, Step B, and substituting Compound 19 for Compound 15. $^1$H NMR (300 MHz, CDCl$_3$): δ 7.7 (s, 1H), 7.3-6.8 (m, 4H), 4.2 (t, 2H), 3.3 (s, 3H), 2.9 (m, 4H), 2.6 (m, 4H), 2.4 (t, 2H), 1.8 (m, 2H), 1.6 (m, 2H). HRMS calcd for C$_{18}$H$_{26}$O$_3$N$_5$ (MH+): 360.2036. Found: 360.2032.

Example 4

Preparation of Compound D

Step A: Preparation of Intermediate Compound 21

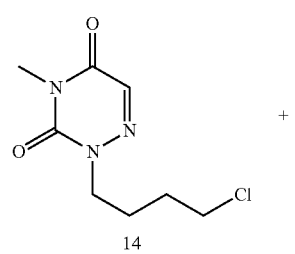

14

+

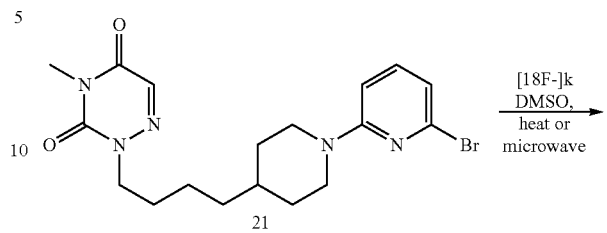

20

(Et)$_3$N, nBuOH

21

Intermediate compound was made using a method identical to compound 15 described in Example 1. $^1$H NMR (400 MHz, CDCl$_3$) d: 1.58-1.63 (m, 2H); 1.84 (pentet, 2H, J=7.6 Hz); 2.44 (t, 2H, J=7.6 Hz); 2.54 (t, 4H, J=5.2 Hz); 3.37 (s, 3H); 3.56 (t, 4H, J=4.8 Hz); 4.05 (t, 2H, J=7.2 Hz); 6.53 (d, 1H, J=8.4 Hz); 6.76 (d, 1H, J=7.2 Hz); 7.33 (dd, 1H, J=7.6, 8.0 Hz); 7.42 (s, 1H).

Step B: Radiolabeling of Compound 21 to Provide Compound D:

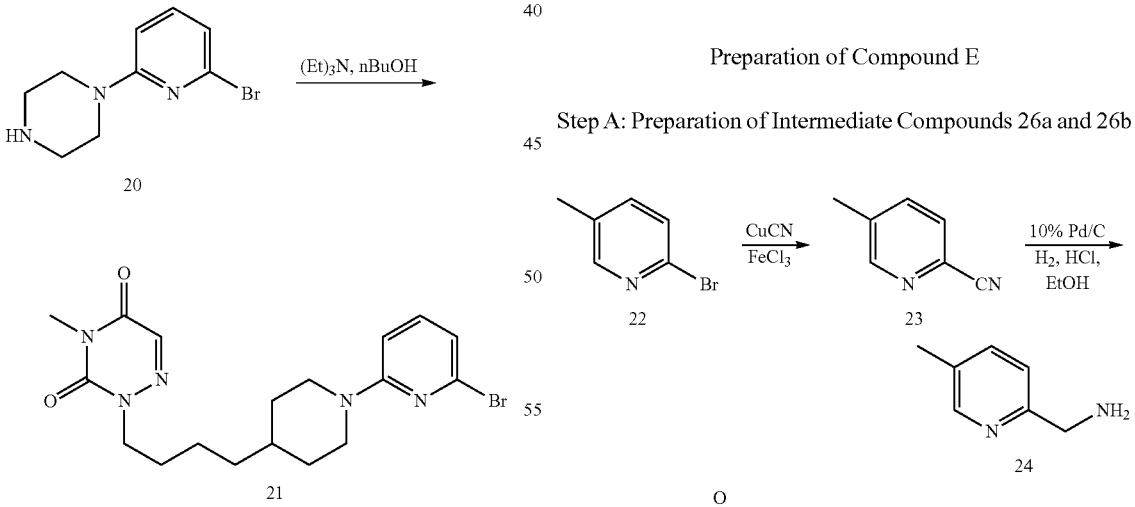

D

The precursor compound 21 (1.0 mg) may then be dissolved in 400 µL of DMSO and transferred to a reaction vessel containing azeotropically dried [$^{18}$F]$^-$, KRYPTOFIX, and K$_2$CO$_3$. The reaction mixture may be heated at 100° C. for 15 minutes, cooled down, and diluted with 0.5 mL of water and injected onto a semi preparative RP-HPLC (Phenomenex C18, 10×250 mm, 10µ). The product fraction based on a γ-detector may be collected, diluted with 100 mL of deionized water, and passed through a classic C-18 Sep-Pak cartridge. Reconstruction of the product in 1 mL of absolute ethanol provides Compound D. A microwave can also be used instead of heating at 100° C. for 15 minutes.

Example 5

Preparation of Compound E

Step A: Preparation of Intermediate Compounds 26a and 26b

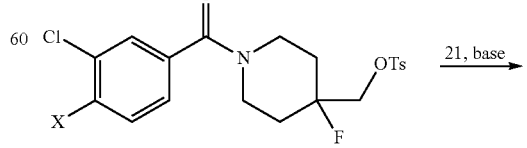

25a X = NO2
25b X = F

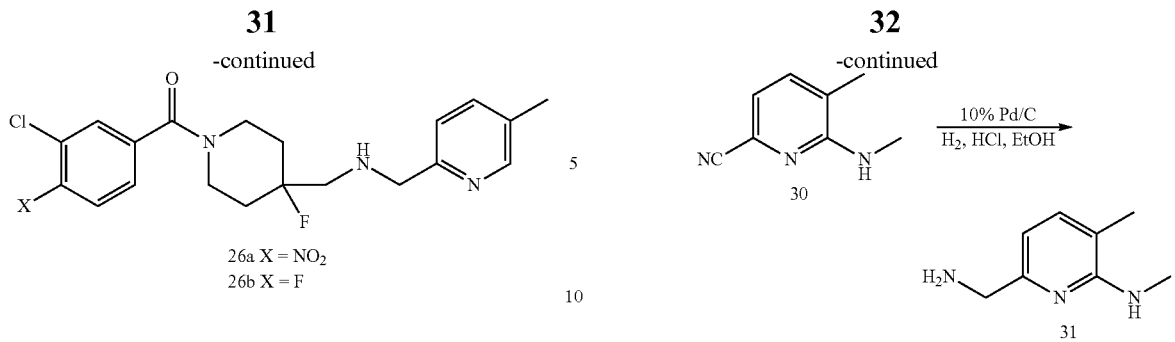

Step B: Radiolabeling of Compound 26a to Provide Compound E:

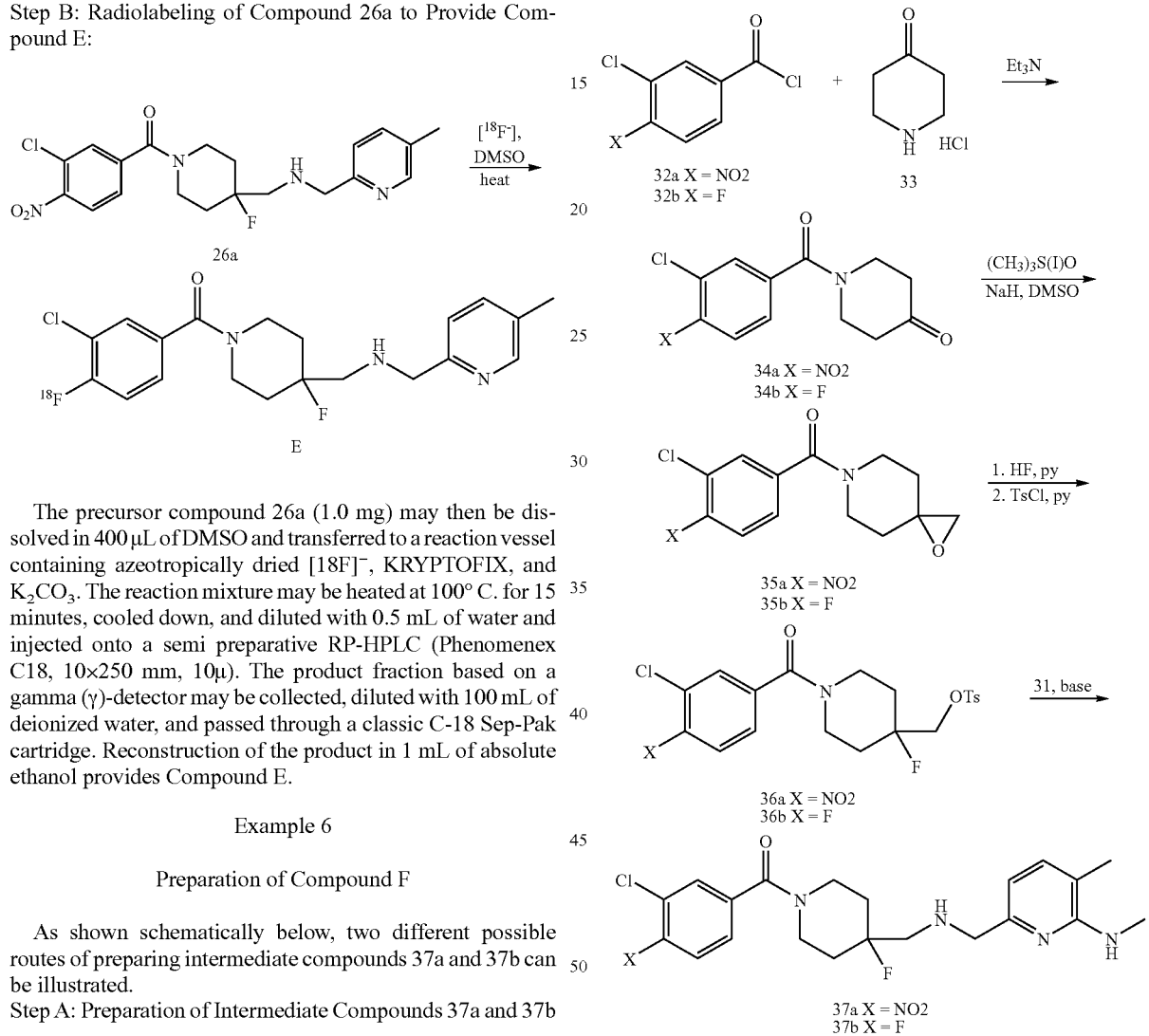

The precursor compound 26a (1.0 mg) may then be dissolved in 400 μL of DMSO and transferred to a reaction vessel containing azeotropically dried [18F]⁻, KRYPTOFIX, and K$_2$CO$_3$. The reaction mixture may be heated at 100° C. for 15 minutes, cooled down, and diluted with 0.5 mL of water and injected onto a semi preparative RP-HPLC (Phenomenex C18, 10×250 mm, 10μ). The product fraction based on a gamma (γ)-detector may be collected, diluted with 100 mL of deionized water, and passed through a classic C-18 Sep-Pak cartridge. Reconstruction of the product in 1 mL of absolute ethanol provides Compound E.

Example 6

Preparation of Compound F

As shown schematically below, two different possible routes of preparing intermediate compounds 37a and 37b can be illustrated.

Step A: Preparation of Intermediate Compounds 37a and 37b

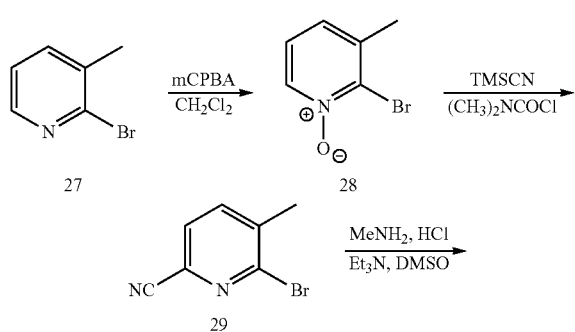

Step B: Alternate Preparation of Intermediate Compounds 37a and 37b

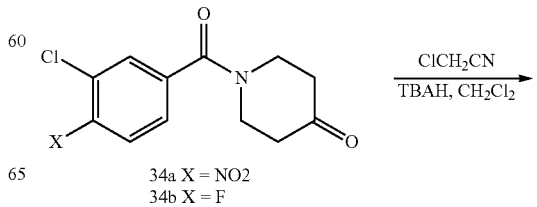

-continued

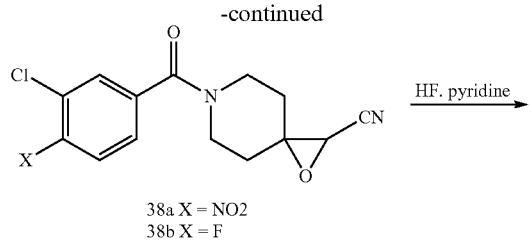

38a X = NO2
38b X = F

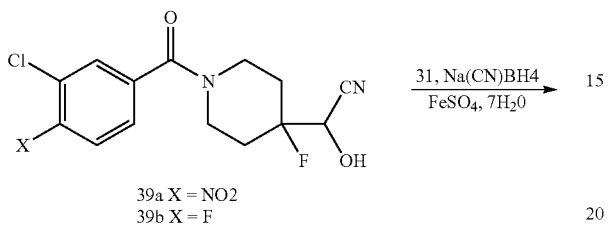

39a X = NO2
39b X = F

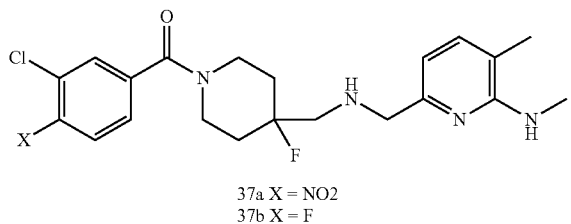

37a X = NO2
37b X = F

Step C: Radiolabeling of Precursor Compound 37a to Provide Compound F:

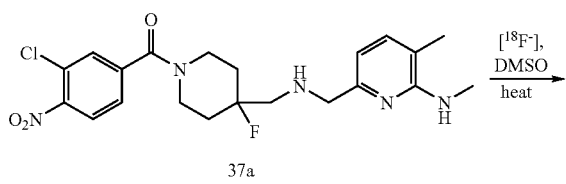

37a

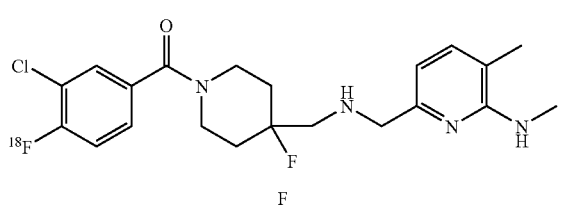

F

Compound F may be prepared using the method described in Example 5, step B, and substituting Compound 37a for Compound 26a.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed:

1. A compound having the formula:

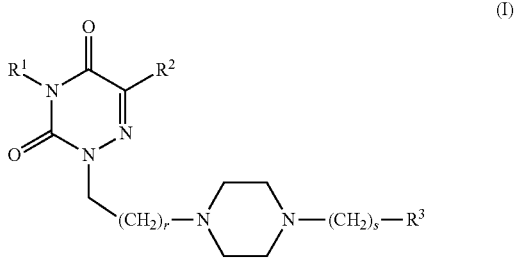

(I)

or a pharmaceutically acceptable salt thereof,
wherein:
r and s are each independently an integer ranging from 0 to 6;
$R^1$ is —H, -aryl, —$C_1$-$C_6$ alkyl, —$C_3$-$C_7$ cycloalkyl, —$C_3$-$C_7$ cycloalkenyl, or -3- to 7-membered heterocycle;
$R^2$ is —H, -aryl, —$C_1$-$C_6$ alkyl, —$C_3$-$C_7$ cycloalkyl, —$C_3$-$C_7$ cycloalkenyl, -3- to 7-membered heterocycle, -halo, —$CF_3$, —$C_2$-$C_6$ alkenyl, —$C_2$-$C_6$ alkynyl, —$N(R^4)_2$, —CN, —$OR^4$ or —$SR^4$;
$R^3$ is -aryl or -5- to 7-membered aromatic heterocycle, each of which is substituted with one $R^6$ group and optionally substituted with one or more of the following groups: —$C_1$-$C_6$ alkyl, —$C_3$-$C_7$ cycloalkyl, —$C_3$-$C_7$ cycloalkenyl or -3- to 7-membered heterocycle, -halo, —$CF_3$, —$C_2$-$C_6$ alkenyl, —$C_2$-$C_6$ alkynyl, —($C_1$-$C_6$ alkylene)-aryl, —$N(R^4)_2$, —CN, —$OR^4$, —$SR^4$, —S(O)—$R^4$, —$SO_2$—$R^4$, —$SO_2NH$—$R^4$, —$SO_3H$, —NH—$SO_2$—$R^4$, —C(O)$R^5$ or —NHC(O)$R^5$;
each occurrence of $R^4$ is independently —H, —$C_1$-$C_6$ alkyl, —$C_2$-$C_6$ alkenyl, —$C_2$-$C_6$ alkynyl, -aryl, —($C_1$-$C_6$ alkylene)-aryl, —$C_3$-$C_7$ cycloalkyl, —$C_3$-$C_7$ cycloalkenyl or -3- to 7-membered heterocycle;
$R^5$ is —$R^4$, —$N(R^4)_2$ or —$OR^4$;
$R^6$ is -M-Q, —O-M-Q, —S-M-Q, —NH-M-Q, —F, —$^{18}$F, —$^{18}$F-labeled $CF_3$, —$CF_2H$, —$^{18}$F-labeled $CF_2H$, or —$^{11}$C-labeled CN;
M is —$^{11}$C-labeled $C_1$-$C_6$ alkylene-, —$^{11}$C-labeled $C_2$-$C_6$ alkenylene-, —$^{11}$C-labeled $C_2$-$C_6$ alkynylene-, —$^{18}$F-labeled $C_1$-$C_6$ alkylene-, —$^{18}$F-labeled $C_2$-$C_6$ alkenylene-, or —$^{18}$F-labeled $C_2$-$C_6$ alkynylene-;
Q is —H or -aryl.

2. The compound of claim 1, wherein $R^1$ is —$C_1$-$C_6$ alkyl.
3. The compound of claim 2, wherein $R^1$ is methyl.
4. The compound of claim 1, wherein $R^2$ is —H.
5. The compound of claim 4, wherein $R^1$ is methyl.
6. The compound of claim 1, wherein $R^3$ is aryl.
7. The compound of claim 6, wherein $R^3$ is naphthyl.
8. The compound of claim 6, wherein $R^6$ is —O—$^{11}CH_3$.
9. The compound of claim 1, wherein r is 3.
10. The compound of claim 1, wherein s is 0.
11. The compound of claim 1, wherein r is 3 and s is 0.
12. The compound of claim 7, wherein r is 3 and s is 0.

13. The compound of claim 1 having the formula:

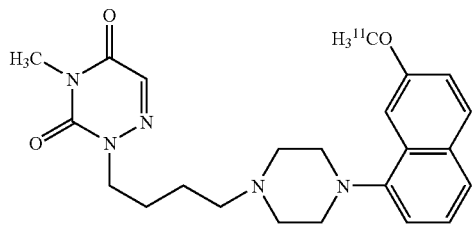

or a pharmaceutically acceptable salt thereof.

14. The compound of claim 1 having the formula:

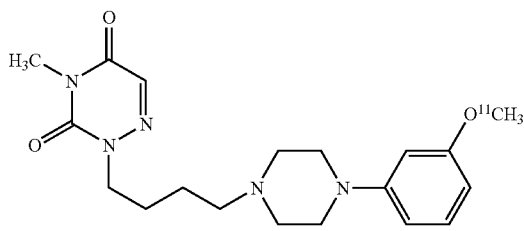

or a pharmaceutically acceptable salt thereof.

15. The compound of claim 1 having the formula:

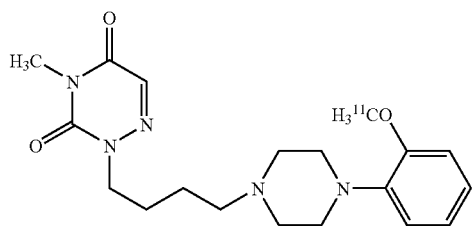

or a pharmaceutically acceptable salt thereof.

16. The compound of claim 1 having the formula:

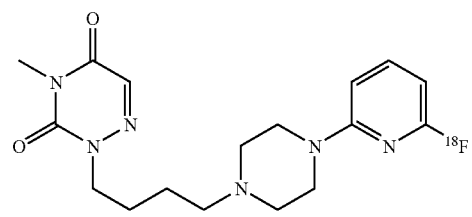

or a pharmaceutically acceptable salt thereof.

17. A compound of claim 1, wherein the compound is radiolabeled.

18. A compound of claim 1, wherein the compound is not radiolabeled.

19. A composition comprising an imaging-effective amount of a compound of claim 17 or a pharmaceutically acceptable salt thereof, and a physiologically acceptable carrier or vehicle.

20. A method for imaging one or more 5-HT$_{1A}$ receptors in a subject in vivo, in need thereof, the method comprising:
    (a) administering to the subject an imaging-effective amount of the compound or a pharmaceutically acceptable salt of the compound of claim 17; and
    (b) detecting the radioactive emission of the compound or salt thereof administered to the subject.

21. The method of claim 20, wherein the compound of claim 17 is:

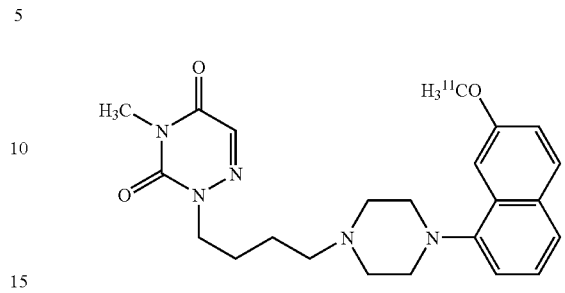

or a pharmaceutically acceptable salt thereof.

22. The method of claim 20, wherein the compound of claim 17 is:

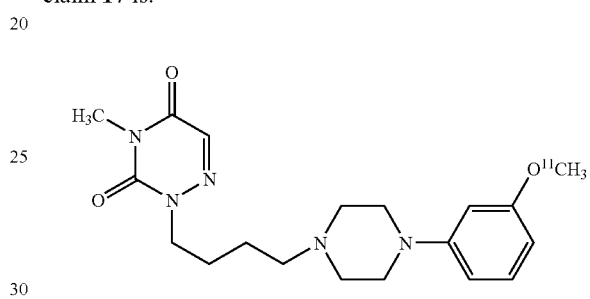

or a pharmaceutically acceptable salt thereof.

23. The method of claim 20, wherein the compound of claim 17 is:

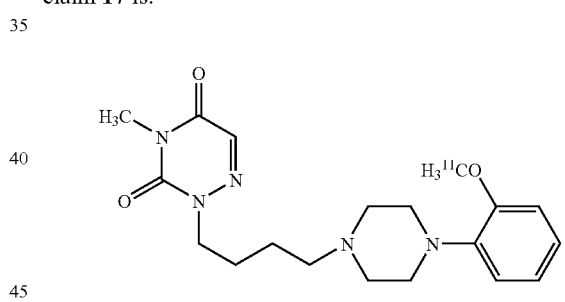

or a pharmaceutically acceptable salt thereof.

24. The method of claim 20, wherein the compound of claim 17 is:

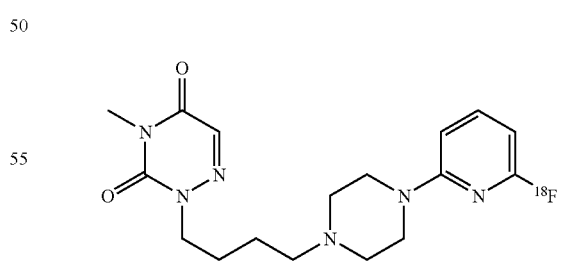

or a pharmaceutically acceptable salt thereof.

25. The method of claim 20, wherein the radioactive emission is detected using positron-emission tomography.

26. The method of claim 20, wherein the radioactive emission is detected in the brain of the subject.

27. The method of claim 20, wherein the subject is known or suspected to have a neurological disorder.

28. The method of claim 27 wherein the neurological disorder is a disease associated with cognitive dysfunction, a neurodegenerative disease, such as stroke; a seizure disorder, a pain disorder; or a disorder of movement.

29. The method of claim 28, wherein the disease associated with cognitive dysfunction is Alzheimer's disease.

30. The method of claim 28, wherein the neurodegenerative disease is multiple sclerosis or amyotrophic lateral sclerosis.

31. The method of claim 28, wherein the disorder of movement is Parkinson's disease.

32. The method of claim 28, wherein the seizure disorder is epilepsy.

33. The method of claim 28, wherein the affective disorder is depression.

34. The method of claim 20, wherein the compound of claim 17 selectively binds to the 5-$HT_{1A}$ receptor relative to other serotonin receptors.

35. A composition comprising a physiologically acceptable salt and the compound or pharmaceutically acceptable salt of the compound of claim 1.

36. The method of claim 20, wherein the subject is known or suspected to have a psychiatric disorder selected from the group consisting of major depressive disorder, bipolar disorder, bulimia nervosa, panic disorder, premenstrual dysphoric disorder, chronic fatigue syndrome, post-traumatic stress disorder, social anxiety disorder, an eating disorder, addictive disorder, a sleep disorder, an affective disorder, obsessive-compulsive disorder, and anxiety disorder.

37. A method of pre-screening subjects to determine whether the subject is likely to respond to medicinal agents which bind 5-HT receptors, comprising administration of a radiolabeled compound of claim 17.

* * * * *